US006638528B1

United States Patent
Kanios

(10) Patent No.: US 6,638,528 B1
(45) Date of Patent: Oct. 28, 2003

(54) COMPOSITIONS AND METHODS TO EFFECT THE RELEASE PROFILE IN THE TRANSDERMAL ADMINISTRATION OF ACTIVE AGENTS

(75) Inventor: David Kanios, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 10/086,457

(22) Filed: Mar. 1, 2002

Related U.S. Application Data

(63) Continuation of application No. 09/765,932, filed on Jan. 19, 2001, now abandoned.
(60) Provisional application No. 60/177,103, filed on Jan. 20, 2000.

(51) Int. Cl.[7] .................... A61K 9/70; A61K 13/00
(52) U.S. Cl. .................. 424/449; 424/448; 424/443; 424/484
(58) Field of Search ................... 424/448, 449, 424/484, 487, 488, 443

(56) References Cited

U.S. PATENT DOCUMENTS

| | | |
|---|---|---|
| 4,584,355 A | 4/1986 | Blizzard et al. |
| 4,585,836 A | 4/1986 | Homan et al. |
| 4,591,622 A | 5/1986 | Blizzard et al. |
| 4,638,043 A | 1/1987 | Szycher et al. |
| 4,655,767 A | 4/1987 | Woodard et al. |
| 4,746,509 A | 5/1988 | Haggiage et al. |
| 4,839,174 A | 6/1989 | Baker et al. |
| 4,840,796 A | 6/1989 | Sweet et al. |
| 4,842,864 A | 6/1989 | Guillemet et al. |
| RE32,991 E | 7/1989 | Szycher et al. |
| 4,883,669 A | 11/1989 | Chien et al. |
| 4,900,554 A | 2/1990 | Yanagibashi et al. |
| 4,994,267 A | 2/1991 | Sablotsky |

(List continued on next page.)

FOREIGN PATENT DOCUMENTS

| | | |
|---|---|---|
| EP | 0 224 981 | 6/1987 |
| EP | 0 697 860 | 4/1994 |
| EP | 913 158 | 6/1999 |
| WO | WO94/06436 | 3/1994 |
| WO | WO94/26257 | 11/1994 |
| WO | WO95/22322 | 8/1995 |
| WO | WO95/31188 | 11/1995 |
| WO | WO96/21433 | 7/1996 |
| WO | WO98/17263 | 4/1998 |
| WO | WO98/31349 | 7/1998 |
| WO | WO98/39042 | 9/1998 |
| WO | WO99/55286 | 11/1999 |
| WO | WO00/59483 | 10/2000 |
| WO | WO00/74661 | 12/2000 |
| WO | PCT/US01/01999 | 8/2001 |

OTHER PUBLICATIONS

Dow Chemical Company, "Product Specification Sheet for Ethocel FP Polymers," Oct. 1998, U.S.A.

Dow Chemical Company, "Bibliography: ETHOCEL Ethylcellulose in Pharmaceuticals," Jun. 1996, U.S.A.

(List continued on next page.)

*Primary Examiner*—Thurman K. Page
*Assistant Examiner*—Robert M. Joynes
(74) *Attorney, Agent, or Firm*—Jay G. Kolman, Esq.

(57) ABSTRACT

Compositions and methods for the transdermal delivery of active agents up to a period of seven days or more at substantially a zero-order release rate comprising a pharmaceutically acceptable adhesive matrix and a polymeric plastic material that provides a release rate regulating effect on the active agents.

6 Claims, 6 Drawing Sheets

U.S. PATENT DOCUMENTS

| | | |
|---|---|---|
| 5,118,779 A | 6/1992 | Szycher |
| 5,176,915 A | 1/1993 | Hoffmann |
| 5,232,702 A | 8/1993 | Pfister et al. |
| 5,446,070 A | 8/1995 | Mantelle |
| 5,474,783 A | 12/1995 | Miranda et al. |
| 5,523,095 A | 6/1996 | Wison et al. |
| 5,556,635 A | 9/1996 | Istin et al. |
| 5,656,286 A | 8/1997 | Miranda et al. |
| 5,662,923 A | 9/1997 | Roreger |
| 5,662,926 A | 9/1997 | Wick et al. |
| 5,676,969 A | 10/1997 | Wick et al. |
| 5,679,373 A | 10/1997 | Wick et al. |
| 5,716,609 A | 2/1998 | Jain et al. |
| 5,810,786 A | 9/1998 | Jackson et al. |
| 5,885,612 A | 3/1999 | Meconi et al. |
| 5,904,931 A | 5/1999 | Lipp et al. |
| 5,906,814 A | 5/1999 | Epstein |
| 6,010,715 A | 1/2000 | Wick et al. |
| 6,024,974 A * | 2/2000 | Li .............................. 424/448 |
| 6,143,319 A | 11/2000 | Meconi et al. |
| 6,190,689 B1 | 2/2001 | Hoffmann et al. |
| 6,231,885 B1 | 5/2001 | Carrara |
| 6,274,165 B1 | 8/2001 | Meconi et al. |

OTHER PUBLICATIONS

Dow Chemical Company, "Ethocel Polymers for General Applications," Mar. 1998, U.S.A.

Dow Chemical Company, "Ethocel Premium Polymers for Pharmaceutical Applications," May 1996, U.S.A.

Dow Chemical Company, "Ethocel Premium Ethylcellulose in Pharmaceutical Applications," Dec. 1991, U.S.A.

Wiley–Interscience/John Wiley & Sons, March, Jerry, *Advanced Organic Chemistry: Reactions, Mechanisms, and Structure*, 4th Ed., 1992.

BASF Aktiengesellschaft, Buhler, *Kollidon® Polyvinylpyrrolidone for the Pharmaceutical Industry*, 2nd Ed., Aug. 1993.

Van Nostrand Reinhold, New York, Satas, Donatas, "Acrylic Adhesives," pp. 396–456, 1989, *Handbook of Pressure–Sensitive Adhesive Technology, 2nd Edition*.

Van Nostrand Reinhold, New York, Sobieski, Loretta, et al., "Silicone Pressure Sensitive Adhesives," pp. 508–517; 1989, *Handbook of Pressure Sensitive Adhesive Technology, 2nd Ed.*

* cited by examiner

COMPOSITIONS AND METHODS TO EFFECT THE RELEASE PROFILE IN THE TRANSDERMAL ADMINISTRATION OF ACTIVE AGENTS

CROSS-REFERENCE TO RELATED APPLICATION

This application is a continuation application of U.S. Ser. No. 09/765,932, filed Jan. 19, 2001 now abandoned, which is based on and claims the benefit of Provisional Application No. 60/177,103, filed Jan. 20, 2000. Both of these applications are incorporated in their entirety herein by reference.

FIELD OF THE INVENTION

This invention relates generally to transdermal drug delivery systems, and more particularly to pharmaceutically acceptable adhesive matrix compositions, that use polymeric plastic materials, in particular insoluble cellulose derivatives such as ethyl celluloses, to regulate the drug release profile. The invention additionally relates to transdermal drug delivery systems providing substantially zero order drug release profiles for an extended period of time of up to seven days or longer.

BACKGROUND OF THE INVENTION

The use of transdermal drug delivery systems as a means to topically administer an active agent is well known. Such systems incorporate the active agent into a carrier composition, such as a polymeric and/or pressure-sensitive adhesive composition, from which the active agent is delivered through the skin or mucosa of the user.

In general, transdermal drug delivery systems are either reservoir-type or matrix-type devices. Both types of devices employ a backing layer that forms the protective outer surface of the finished transdermal system and which is exposed to the environment during use, and a release liner or protective layer that forms the inner surface and which covers whatever adhesive means is employed for affixing the system to the skin or mucosa of a user. The release liner or protective layer is removed prior to application, exposing the adhesive means, which is typically a pressure-sensitive adhesive.

In the "classic" reservoir-type device, the active agent is usually dissolved or dispersed in a carrier that typically yields a non-finite carrier form, like a fluid or gel, and which is kept separate from the adhesive means used to affix the device to the user. The device has a pocket or "reservoir" which physically serves to hold the active agent and carrier, and which is formed in or by the backing layer itself. A peripheral adhesive layer is then used to affix the device to the user. The early reservoir-type devices incorporated drugs which were readily absorbed through the skin like nitroglycerin and nicotine.

Such devices have a number of disadvantages including a non-uniform drug release profile wherein a high dose of drug is released initially upon application to the user, often described as a "burst effect." This burst or high initial release of drug then drops off after a period of time to a rate that is less than is able to achieve a therapeutically effective amount. Drug delivery according to this profile is described as first order release.

While such classic devices are still in use today, the term reservoir is being used interchangeably with matrix-type devices which still rely upon a separate adhesive means used to affix the device to the user.

In a matrix-type device, the active agent is dissolved or dispersed in a carrier that typically yields a finite carrier form, which can be self-adhesive or non-adhesive. Non-adhesive matrix-type devices, that is, those which still rely upon a separate adhesive means to affix the device to the user, employ a drug permeable adhesive layer (often referred to as an "in-line adhesive" since the drug must pass through), applied over the drug matrix carrier layer. In an attempt to better control the release rate of the drug, such devices often employ one or more additional drug permeable layers such as rate controlling membranes, or containing excipients, such as drug delivery enhancers. Hence, such devices are also commonly referred to as multilayer or multilaminate.

In a "monolithic or monolayer" matrix-type device, the active agent is typically solubilized or homogenously blended in an adhesive carrier composition, typically a pressure-sensitive adhesive or bioadhesive, which functions as both the drug carrier and the means of affixing the system to the skin or mucosa. Such devices, commonly referred to as drug-in-adhesive devices, are described, for example, in U.S. Pat. Nos. 4,994,267, 5,446,070, 5,474,783 and 5,656,286, all of which are assigned to Noven Pharmaceuticals, Inc., Miami, Fla.

While matrix-type devices, especially drug-in-adhesive devices, have achieved more uniform and controlled drug deliver rates, and for longer periods of time, most transdermal systems remain subject to a higher initial drug release than is required to achieve therapeutic efficacy. For many drugs and/or therapeutic situations, it would be advantageous to eliminate or suppress this higher initial release and achieve a "steady state" (zero order) release profile which uniformly delivers a therapeutically effective amount of drug over the extended duration of device's desired use.

For example, the high initial release of certain drugs may cause adverse or undesired effects, or create toxicity concerns, thereby foreclosing the use of transdermal administration. In other instances, the higher initial release may reduce the amount of drug required for treatment to the point of risking underdosing, or may make it impractical to try and increase the duration of the device's application while retaining therapeutic effectiveness. The ability to reduce the frequency of replacing the transdermal drug delivery system would concomitantly increase user compliance, reduce any lag or drop off in efficacious. blood levels, and reduce the amount of drug required for treatment (also provided by reducing the higher initial blood level associated with the higher release rate).

Therefore, despite the existence of many different types of transdermal delivery systems in the art, there remains a continuing need for improving the release profile of drugs to achieve substantially zero order, as well as extending the duration of use of each transdermal system.

U.S. Pat. Ser. No. 07/897,269 discloses the use of glycerin to counteract the burst effect of drugs in transdermal formulations.

It has now been found that the addition of certain polymeric plastic polymers, in particular insoluble cellulose derivatives such as ethyl celluloses, into a pressure-sensitive adhesive matrix composition, eliminates or suppresses the initial high release rate of a drug subject to a first order release rate profile such that the system achieves substantially zero order release, and is able to maintain a substantially zero order release profile for an extended period of time up to seven days or longer.

Although not wishing to be bound by theory, particularly in this case where the structure of the composition has not been analyzed, it is postulated that the insoluble polymeric plastic material affects the uptake/absorption of water or moisture from the application site into the matrix composition which would otherwise create some of the kinetic driving force for release of the drug. This appears especially significant in the presence of hydrophobic drugs and/or in conjunction with the use of hydrophilic crystallization inhibitors, such as polyvinylpyrrolidones.

Ethyl celluloses have been extensively used in industrial applications since their commercial introduction in the mid-1930s. They are recognized and widely used as well for many different purposes in pharmaceutical applications, especially in conjunction with water-sensitive ingredients. Ethyl celluloses are most frequently used as binders, fillers, flavor fixatives, controlled release coatings/barriers in microencapsulation and other solid dosage forms, particularly multiparticulate systems, granulation aids, tablet film formers and taste maskers.

The prior art generally discloses the use of insoluble polymers such as ethyl cellulose as optional components in transdermal systems as thickening agents and as cohesiveness strengthening agents which effect the carrier's adhesive properties. For example, U.S. Pat. No. 5,232,702 discloses the use of a variety of substances that include ethyl cellulose and polyvinyl alcohol as cohesive strengthening agents (reducing flow properties of silicone adhesives) in a transdermal delivery system.

The present invention is able to regulate the release profile of the drug in a transdermal system without modifying the adhesive properties of the pressure-sensitive adhesive matrix so that the transdermal system possesses the required degree of adhesion and tackiness to remain affixed to the site of application for extended periods of time, which can be seven days or more, but at the same time can be easily removed as required.

The prior art further generally discloses the use of insoluble polymers in transdermal systems as the non-adhesive matrix carrier itself, and even as a "suitable adhesive" for the matrix carrier itself (but which presumably includes the addition of a plasticizer or tackifier, or plasticizing liquid drug like nicotine, to create stickiness since such polymers are not adhesives). For example, U.S. Pat. No. 6,010,715 discloses the use of thermoplastic polymers that are melt-blended with active agents and enhancers that are heat stable at the melt temperature of the polymer. The melt-blend can then be thermoformed into carrier layers without the use of common solvents to produce a controlled release layer in a transdermal drug delivery system. Cellulose derivatives such as ethyl cellulose are generally disclosed as "suitable adhesives" for use as the matrix.

U.S. Pat. No. 5,904,931 discloses the use of ethyl cellulose as a crystallization inhibitor in a transdermal drug delivery system. Cellulose ether and polyvinyl compounds are generally described as additional matrix additives.

SUMMARY OF THE INVENTION

It is therefore an objective of the present objective to provide for methods and pharmaceutically acceptable flexible, finite compositions and systems for the transdermal administration of active agents that achieve a substantially zero-order release profile when applied to a user.

It is another object of the invention to provide an adhesive matrix-type transdermal drug delivery system which achieves a substantially zero-order release profile of the active agent by incorporating a polymeric plastic material into an adhesive drug matrix.

It is still another object of the invention to achieve a substantially zero-order release profile of the active agent for an extended period of time of up to seven days or longer, and effectively continue to deliver the active agent in a therapeutically effective amount.

It is a further object of the invention to provide a method of eliminating or suppressing the high initial release or burst of active agent from an adhesive matrix type transdermal drug delivery system containing a drug subject to a first order release profile.

It is yet another object of the invention to provide a transdermal drug delivery system that can deliver an active agent at substantially zero-order for an extended period of time in excess of 72 hours and up to seven days or more without substantially increasing the surface area of the transdermal delivery system.

DETAILED DESCRIPTION OF THE INVENTION

Figure 1:
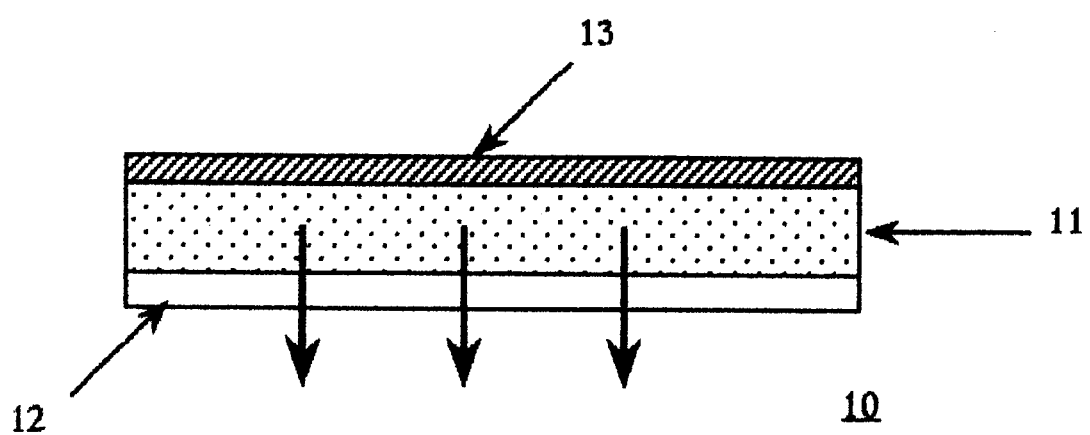
FIG. 1 is a schematic illustration of a matrix-type transdermal drug delivery system of the present invention.
Figure 2:
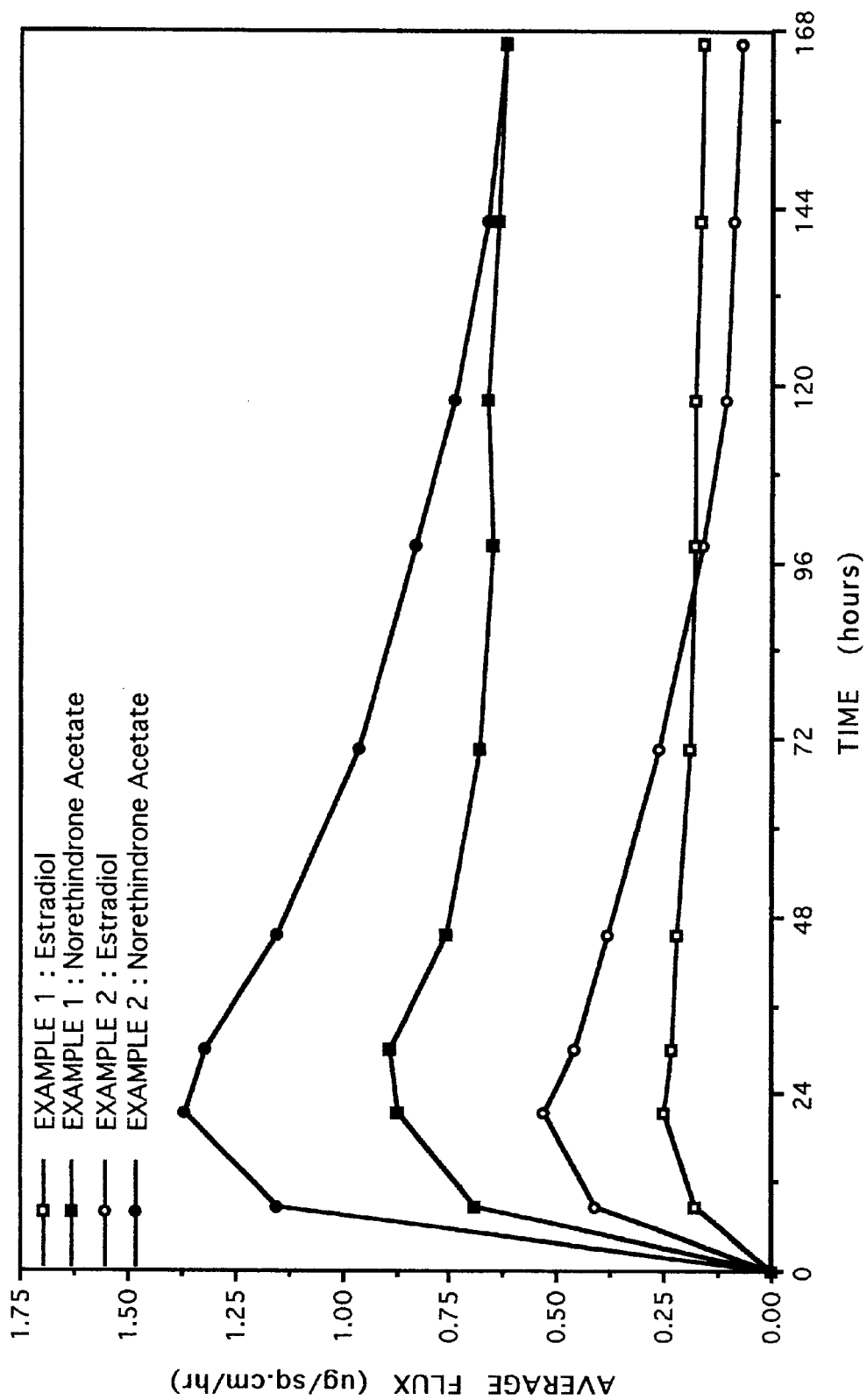
FIG. 2 is a graphical representation comparing the in vitro flux rate of estradiol and norethindrone acetate through cadaver skin from a pressure-sensitive adhesive matrix composition of the present invention with the flux rate for a composition of the prior art.
Figure 3:
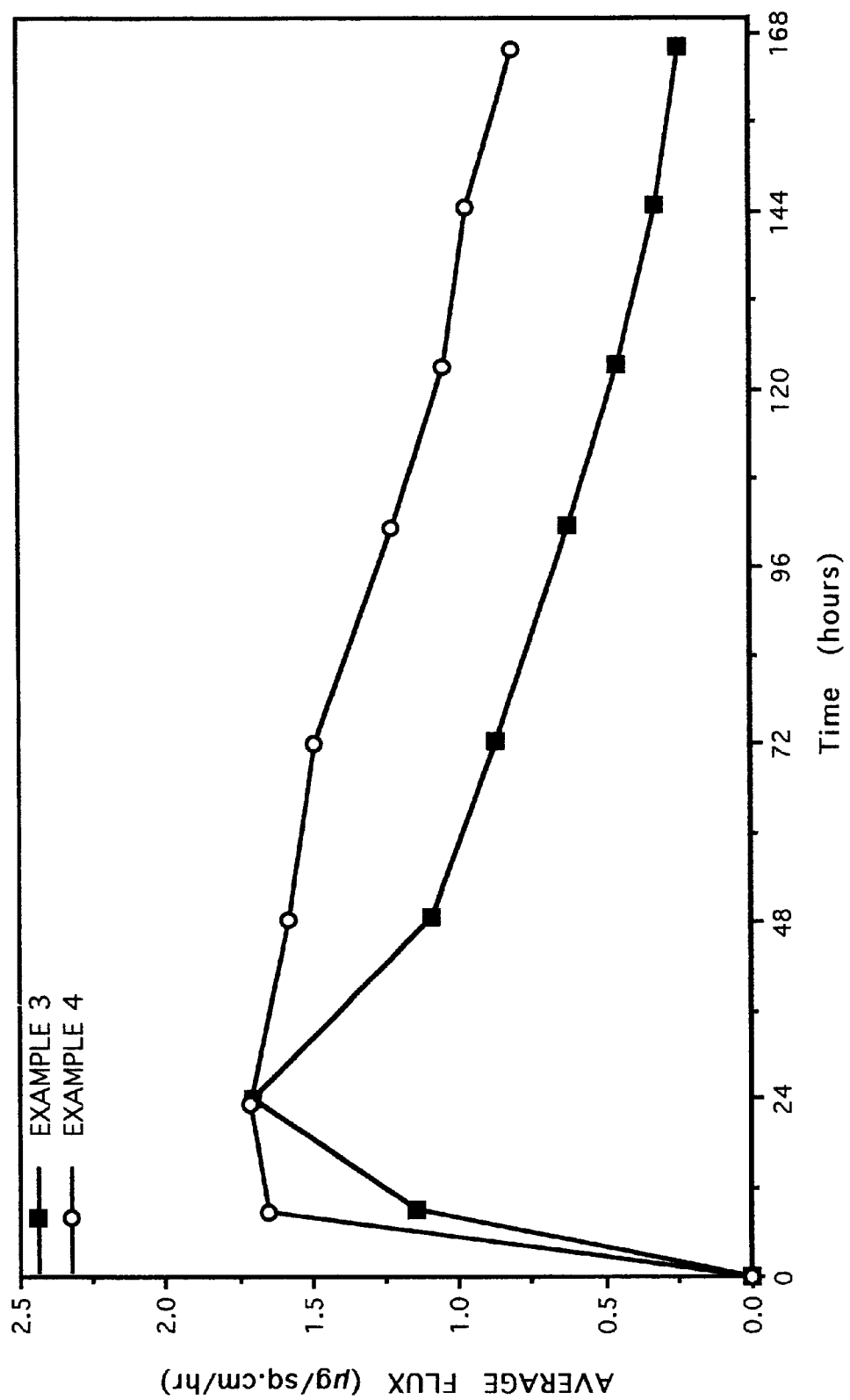
FIG. 3 is a graphical representation of the in vitro first order flux rate of estradiol through cadaver skin from a transdermal drug delivery system of the prior art as compared to the in vitro steady state flux rate of estradiol through cadaver skin from an transdermal drug delivery system of the present invention.
Figure 4:
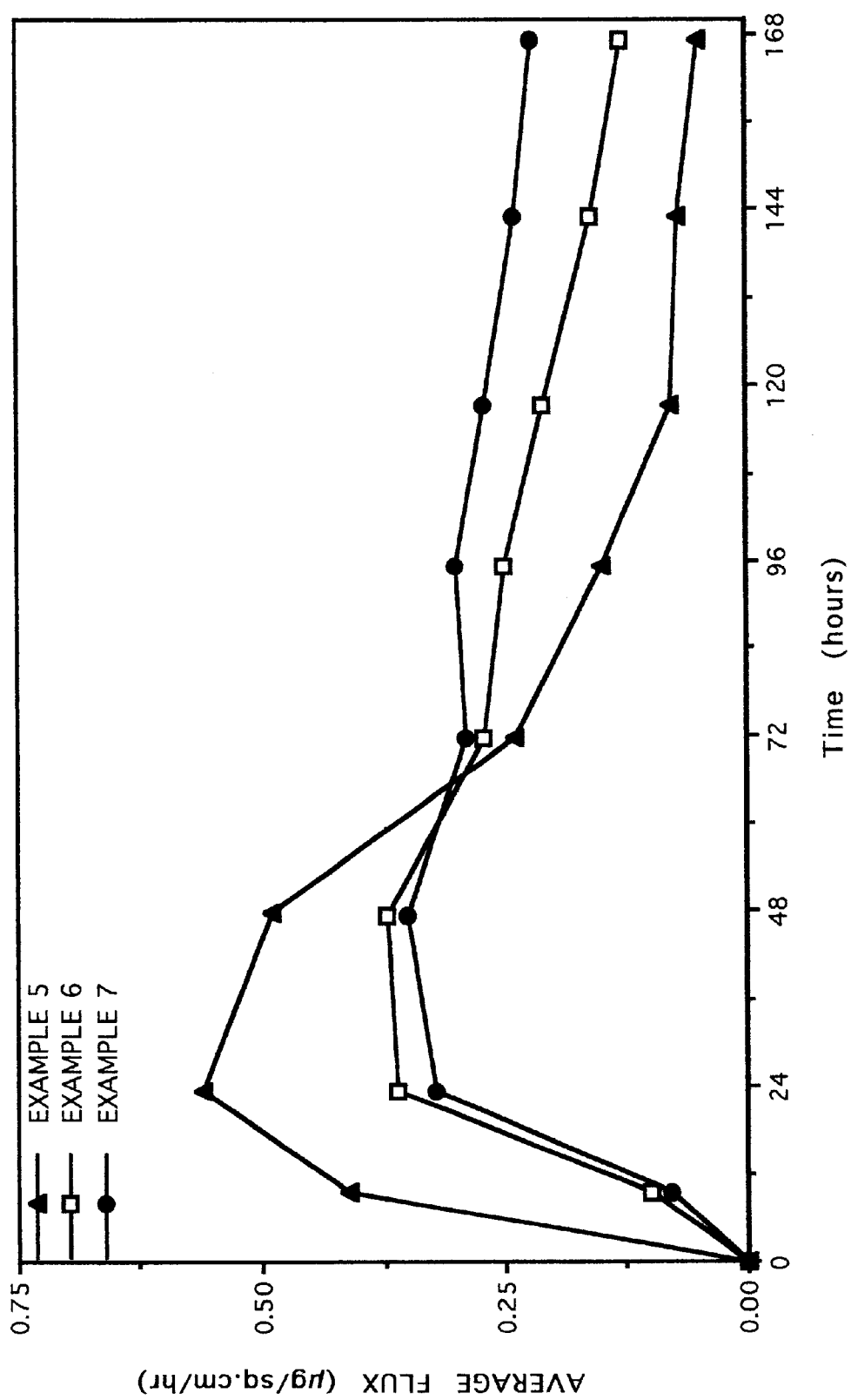
FIG. 4 is a graphical representation of the in vitro flux rates of estradiol through cadaver skin from two pressure-sensitive adhesive matrix compositions of the present invention using various amounts of ethyl cellulose as compared to the in vitro flux rate of estradiol from a pressure-sensitive adhesive matrix composition without ethyl cellulose.
Figure 5:
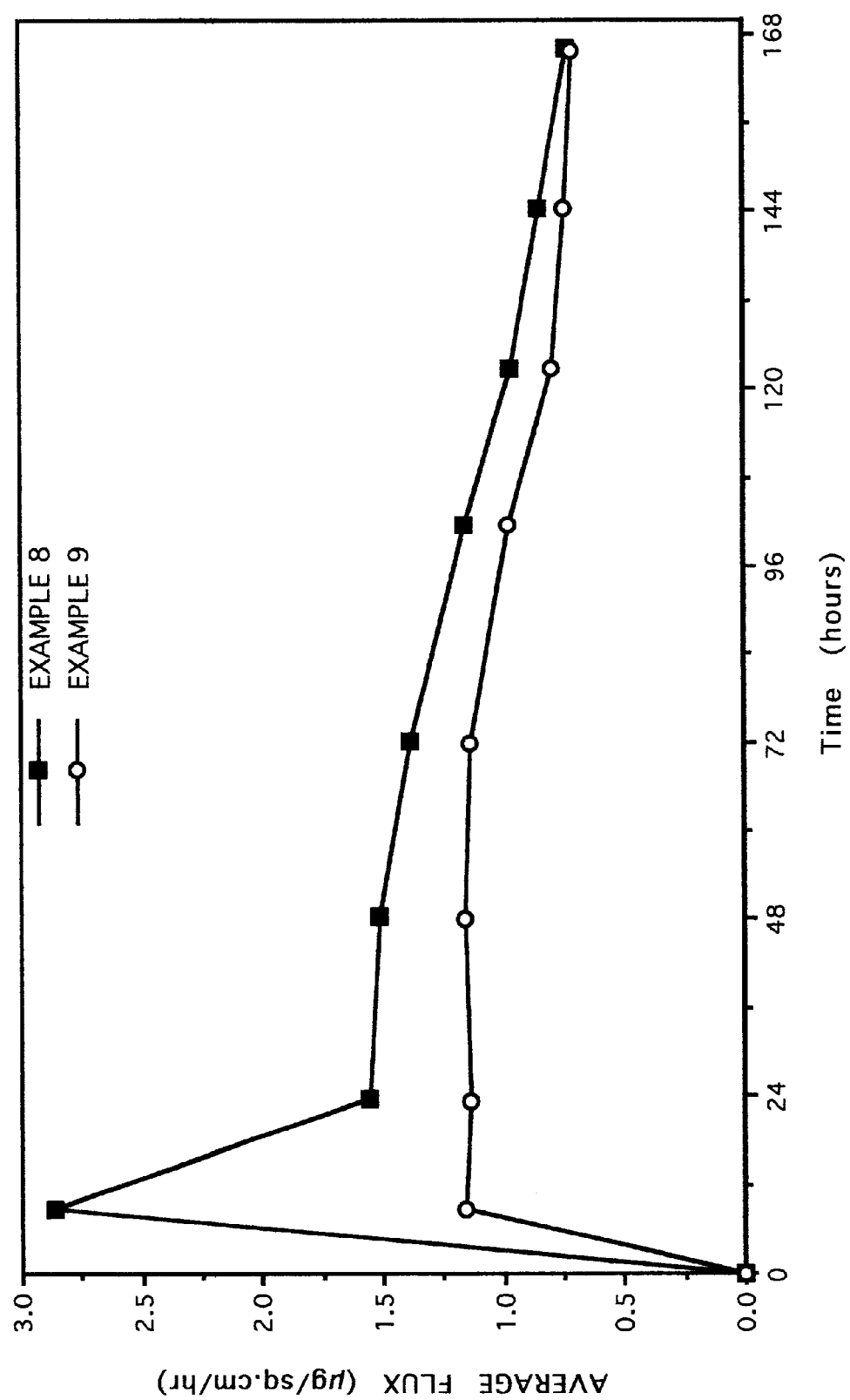
FIG. 5 is a graphical representation of the in vitro flux rates of estradiol through cadaver skin from pressure-sensitive adhesive matrix compositions of the present invention comparing the effect of varying amounts of ethyl cellulose with varying amounts of estradiol.

The foregoing and other objects are achieved by this invention which provides a transdermal drug delivery system wherein the use of a polymeric plastic material provides a release rate regulating effect on the active agents incorporated into the adhesive matrix composition.

Unless defined otherwise, all technical and scientific terms used herein have the same meaning as commonly understood by one of ordinary skill in the art to which the invention pertains.

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage into and/or through skin or mucosa for localized or systemic delivery of an active agent.

The term "solubilized" is intended to mean that in the carrier composition there is an intimate dispersion or dissolution of the active agent at the crystalline, molecular or ionic level. As such, the active agent is considered herein to be in "non-crystallized" form when in the compositions of the present invention.

As used herein, the term "flux" is defined as the absorption of the drug through the skin or mucosa, and is described by Fick's first law of diffusion:

$$J=-D(dCm/dx),$$

Where J is the flux in g/cm2/sec, D is the diffusion coefficient of the drug through the skin or mucosa in cm2/sec and Dcm/dx is the concentration gradient of the drug across the skin or mucosa.

The phrase "pharmaceutically acceptable flexible, finite" is intended to mean a solid form capable of conforming to a surface to which it is applied, and which is capable of maintaining the contact in such solid form so as to facilitate topical application without adverse physiological response, and without being appreciably decomposed by aqueous contact during use by a subject.

The term "user" or "subject" is intended to include all warm-blooded mammals, preferably humans.

The phrase "substantially zero-order" as used herein means transdermal delivery of an active agent at a release rate which is approximately constant once steady state is attained, typically within 12 to 24 hours after topical application. While variability in blood levels of active agent are contemplated within the scope of this meaning once steady state release is attained, the depletion rate of active agent over the duration of use should typically not exceed about 20% to about 25%.

Any polymeric plastic material may be employed for the present invention provided it is insoluble or substantially insoluble in water, and includes cellulose derivatives such as cellulose acetates, (cellulose acetate butyrate, cellulose acetate propionate, cellulose acetate phthalate, etc.), methyl, ethyl and propyl celluloses; polycarbonates; polystyrenes; alkylacrylates such as polymethyl methacrylate, polyethyl ethacrylate, polyethylene methacrylate and other lower alkyl acrylates; vinyl polymers; polyurethanes; polyacrylonitriles; and mixtures, combinations and multipolymers (copolymers, terpolymers, etc.) thereof.

In preferred embodiments, the polymeric plastic material is a cellulose derivative. Preferred are cellulose esters such as cellulose acetates including cellulose acetate, cellulose acetate butyrate, cellulose acetate phthalate, cellulose acetate propionate, and cellulose ethers.

Copending provisional application, Ser. No. 60/137,827, describes the use of cellulose derivatives, particularly cellulose esters, as drug solubility enhancers in matrix carrier compositions.

Particularly preferred cellulose ethers are ethyl cellulose polymers. Ethyl cellulose polymers can be manufactured in a variety of molecular weights, which translates into a range of viscosities when in solution. In practicing the subject invention, it has been found that solution viscosities ranging from about 3 centipoise to about 49 centipoise are preferred, and more preferably from about 6 centipoise to about 40 centipoise, and optimally from about 6 centipoise to about 22 centipoise (viscosities are for 5% solutions, in 80% toluene and 20% ethanol, measured at 25° C. in an Ubbelohde viscometer). Ethyl cellulose polymers having such solution viscosities exhibit melting point temperatures in the range of about 165° C. to about 200° C. Suitable ethyl cellulose polymers are commercially available and include those sold under the trademark ETHOCEL® by the Dow Chemical Company, Midland, Mich. Preferred ETHOCEL® polymers are ETHOCEL® Standard 7, 10, 14 and 20, Premium or Industrial grades.

A crystallization inhibitor or solubility enhancer may also be employed in the invention, for example polyvinylpyrrolidone polymers, polyethylene oxide, polyacrylic acid, polyvinyl alcohol, silicone dioxide, silica, celluloses and cellulose derivatives such as hydroxymethyl cellulose, hydroxypropyl cellulose, gelatins, gums, starches, dextrins and dextrans, sterols, bile acids and other absorptive agents that possess the capability to absorb and hold water or moisture.

Particularly preferred compounds are PVPs. The term "polyvinylpyrrolidone" or "PVP" refers to a polymer, ether a homopolymer or copolymer, containing vinylpyrrolidone (also referred to as N-vinylpyrrolidone, N-vinyl-2-pyrrolidone and N-vinyl-2-pyrrolidinone) as a monomeric unit. PVP polymers include soluble and insoluble homopolymeric PVPs, and copolymers such as vinylpyrrolidone/vinyl acetate and vinylpyrrolidone/dimethylamino-ethylmethacrylate. The cross-linked hompolymer (such as KOLLIDON® CL from BASF) is insoluble and is generally known in the pharmaceutical industry under the designations polyvinylpolypyrrolidone, crospovidone and PVP. The copolymer vinylpyrrolidone-vinyl acetate is generally known in the pharmaceutical industry under the designations Copolyvidon (e), Copolyvidonum or VP-VAc.

Particularly preferred PVPs are soluble. The term "soluble" when used with reference to PVP means that the polymer is soluble in water and generally is not substantially cross-linked, and has a molecular weight of less than about 2,000,000. See, generally, Buhler, KOLLIDON®: POLYVINYLPRYRROLIDONE FOR THE PHARMACEUTICAL INDUSTRY, BASF Aktiengesellschaft (1992). Soluble PVP polymers have been identified in the pharmaceutical industry under a variety of names, the most commonly used include Povidone, Polyvidon (e), Polyvidonum, poly (N-vinyl-2-pyrrolidinone, poly (N-vinylbutyrolactam), poly (1-vinyl-2-pyrrolidinone, poly [1-(2-oxo-lpyrrolidinyl) ethylene].

The amount and type of PVP required in the preferred embodiments will depend on the quantity and type of drug present in the adhesive matrix composition, as well as the type of adhesives, but can be readily determined through routine experimentation.

Typically, the PVP is present in an amount from about 5% to about 50% by weight, preferably from about 10% to about 40% by weight based on the dry weight of the total adhesive matrix composition. However, the amount of PVP can be higher than 20% for example, up to 40%, depending on the particular drug used and on the desired properties of the matrix blend.

Said PVP preferably has a molecular weight of about 2,000 to 2,000,000, more preferably 5,000 to 100,000, and most preferably 7,000 to 54,000. PVP having a molecular weight of about 1,000,000 to about 1,500,000 is also preferred.

PVPs are sold to the pharmaceutical industry under the trademarks KOLLIDON by BASF (Parsippanny, N.J.); PLASDONE, POLYPLASDONE and COPOLYMER 958 by ISP Technologies, Wayne, N.J. Preferred PVPs are KOLLIDON 12PF, 17PF, 25, 30, 90 and VA-64.

Particularly preferred embodiments of the invention include soluble PVP in a polyacrylate and polysiloxane pressure-sensitive adhesive matrix blend.

The amount and type of polymeric plastic material required in the practice of the invention will depend on the one or more additional materials used in the adhesive matrix composition, and on the amount and type of active agent(s). Generally, the amount of polymeric plastic material to be used is an amount sufficient to deliver a therapeutically effective amount of the active agent at a substantially zero-order kinetic rate of delivery for an extended period of time of at least three days and up to seven days or longer, and to eliminate or suppress the high initial release rate of a drug subject to a first order release profile. Typically, the amount of polymeric plastic material to be used ranges from about 0.5% to about 30%, preferably from about 2.5% to 20%, and more preferably from about 5.0% to 15% by weight based on the dry weight of the total adhesive matrix composition. Amounts greater than 30% typically result in loss of adhesive properties necessary to maintain the system topically for an extended period of time.

The adhesive matrix compositions of the present invention are designed to effectively deliver an active agent in a therapeutically effective amount for an extended period of time up to seven days or longer. As used herein, "therapeutically effective" means an amount of an active agent that is sufficient to achieve the desired local or systemic effect or result, such as to prevent, cure, diagnose, mitigate or treat a disease or condition, when applied topically over the duration of intended use. Seven days is generally the preferred maximum duration for application of a transdermal drug delivery system of the present invention because the site of application is typically adversely affected when occluded for a period of time greater than seven days. However, if a non-occlusive backing material (i.e., permeable to water vapor and/or oxygen) is used, then the transdermal system may be applied for periods longer than seven days without adverse effects occurring, if at all, until a much later time. While delivery of drug by the present invention is preferred for at least a seven-day continuous application, the transdermal system may be used discontinuously (i.e., replaced at any time during rather than at the end of the intended duration of use) since the drug release profile is substantially zero order.

The term "active agent" (and its equivalents "agent," "drug," "medicament" and "pharmaceutical") is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. It should be noted that the active agents can be used singularly or in combinations and mixtures.

There is no limitation on the type of active agent that can be used in this invention. However, active agents that are solid or crystalline at room temperature are preferred over liquid drugs, especially nicotine. Moreover, drug forms other than the free base form are also preferred.

The active agents contained in the adhesive matrix composition can be in different forms such as pharmaceutically acceptable salts, bases, esters, amides or pro-drugs, or may be modified by appending one or more appropriate functionalities to enhance selected physical or biological properties, for example as neutral molecules, components of molecular complexes or free bases to improve solubility or release characteristics; or as pharmaceutically acceptable ethers, esters, amides and the like which have desirable retention and release characteristics but which are easily metabolized at body pH.

Compounds may be converted into pharmaceutically acceptable salts, and the salts may be converted into pharmaceutically acceptable free compound using standard procedures known to those skilled in the art of synthetic organic chemistry and described, for example, by J. March, *Advanced Organic Chemistry: Reactions, Mechanisms and Structure*, $4^{th}$ Ed. (New York: Wiley-Interscience, 1992). Acid addition salts are prepared from the free base (e.g., compounds having a neutral —$NH_2$ or cyclic amine group) using conventional means, involving reaction with a suitable acid. An acid addition salt may be converted to the free base by treatment with a suitable base. Basic salts of acid moieties which may be present (e.g., carboxylic acid groups) can be prepared in a similar manner using pharmaceutically acceptable inorganic or organic bases. Compounds may also be converted into pharmaceutically acceptable esters. Suitable esters include branched or unbranched, saturated or unsaturated $C_1$ to $C_6$ alky esters, for example, methyl, ethyl and vinyl esters. Preparation of esters involves functionalization of hydroxyl and/or carboxyl groups which may be present. Pharmaceutically acceptable esters may be prepared using methods known to those skilled in the art and/or described in the pertinent literature. Esters can be reconverted to the free acids, if desired, by using conventional hydrogenolysis or hydrolysis procedures. Preparation of amides and pro-drugs can be performed in an analogous manner.

Steroids and hormonal active agents (including both natural, semi-synthetic and synthetic compounds and their derivatives having steroidal or hormonal activity) are preferred and include, for example, (a) estrogens such as Colpormon, Conjugated Estrogens, Estradiol (17β- and α-) and its Esters (e.g., Acetate, Benzoate, Cypionate, Dipropionate Diacetate, Enanthate, Estradiol-16,17-Hemisuccinate, Undececenoate, Undecylate and Valerate), Estriol, Estrone, Ethinyl Estradiol, Equilenin, Equilin, Mestranol, Methyl Estradiol, Moxestrol, Mytatrienediol, Quinestradiol, Quinestrol, Dienestrol, Clomifen, Chlorotrianisen, and Cyclofenil; (b) progestagenically effective hormones such as Allylestrenol, Anagestone, Chlormadinone Acetate, Delmadinone Acetate, Demegestone, Desogestrel, 3-Keto Desogestrel, Dimethisterone, Dydrogesterone, Ethinylestrenol, Ethisterone, Ethynodiol (and Diacetate), Flurogestone Acetate, Gestodene, Gestonorone Caproate, Haloprogesterone, (17-Hydroxy- and 17-Acetate-) 16-Methylene-Progesterone, 17α-Hydroxyprogesterone (Acetate and Caproate), Levonorgestrel, Lynestrenol, Medrogestone, Medroxyprogesterone (and Acetate), Megestrol Acetate, Melengestrol, Norethindrone (Acetate and Enanthate), Norethisterone, Norethynodrel, Norgesterone, Norgestimate, Norgestrel, Norgestrienone, 19-Norprogesterone, Norvinisterone, Pentagestrone, Progesterone, Promegestone, Quingestrone and Trengestone; and (c) androgenically effective hormones such as Aldosterone, Androsterone, Boldenone, Cloxotestosterone, Dehydroepiandrosterone, Fluoxymesterone, Mestanolone, Mesterolone, Methandrostenolone, Methyltestosterone, 17α-Methyltesteosterone, 17α-Methyltestosterone 3-Cyclopentyl Enol Ether, Norethandrolone, Normethandrone, Oxandrolone, Oxymesterone, Oxymetholone, Prasterone, Stanlolone, Stanozolol, Testosterone (Acetate, Enanthate, Isobutyrate, Propionate and Undecanoate), Testosterone 17-Chloral Hemiacetal, Testosterone 17β-Cypionate and Tiomesterone.

The adhesive matrix composition of the invention preferably contains 17β-estradiol or ethinyl estradiol as the estrogen alone, or in combination with, Norethindrone (Acetate and Enanthate) or Norethisterone, as the progestagen, and mixtures thereof.

In embodiments containing combinations and mixtures of estrogens and progestagens, the use of combinations and mixtures of cellulose derivatives, particularly cellulose esters and ethers, provide improved drug release profiles for an extended period of time as compared to an adhesive matrix composition containing either one alone or none. Preferred combinations or mixtures of cellulose esters and ethers are ethyl cellulose with cellulose acetate butyrate or with cellulose acetate propionate. When used in combinations and mixtures, the amount of each such polymer typically ranges from about 2.5% to about 10% by weight based on the dry weight of the total adhesive matrix composition. Particularly preferred embodiments of such mixtures and combinations include soluble PVP, and typically in an amount of about 5% to about 15% by weight based on the dry weight of the total adhesive matrix composition.

Figure 6:
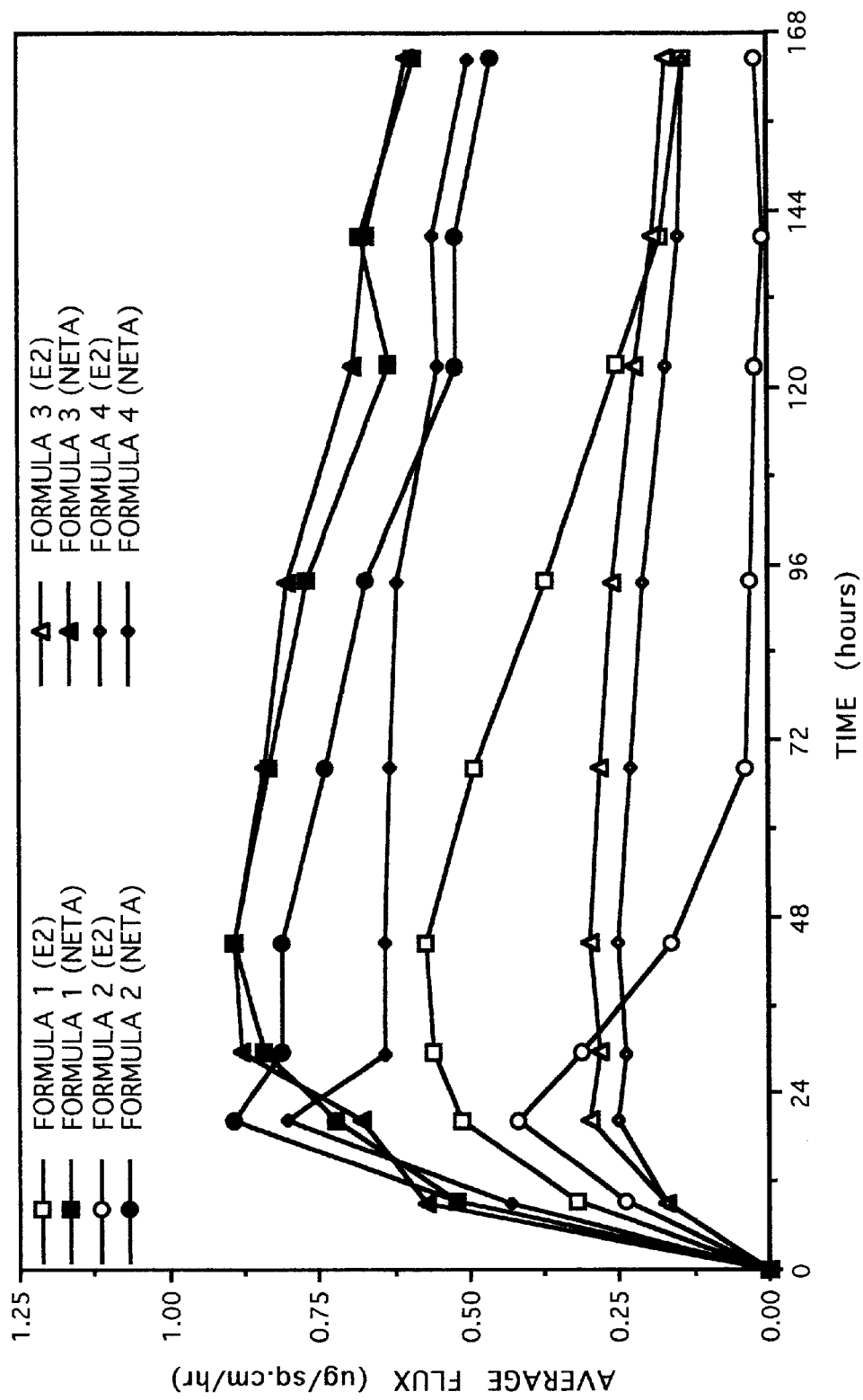
FIG. 6 is a graphical representation of the in vitro flux rates of estradiol and norethindrone acetate through cadaver skin from pressure-sensitive adhesive matrix compositions comparing the effect of using a combination of ethyl cellulose and cellulose acetate butyrate versus either polymer alone.

As shown in FIG. 6, in pressure-sensitive adhesive matrix compositions containing both 17β-estradiol (E$_2$) and norethindrone acetate (NETA) in a polyacrylate/polysiloxane adhesive blend with 10% PVP, Formula 4 comprising 5.0% ethyl cellulose and 5.0% cellulose acetate butyrate demonstrated an improved release profile as compared to either Formula 1 (only 10% PVP), Formula 2 (5.0% ethyl cellulose) or Formula 3 (5.0% cellulose acetate butyrate). The foregoing formulas were prepared using the method of Example 1 to yield the following ingredient concentrations set forth in tabular form in TABLE I.

TABLE I

|  | Formula 1 | Formula 2 | Formula 3 | Formula 4 |
| --- | --- | --- | --- | --- |
| Polysiloxane Adhesive (BIO-PSA ® 7-4603) | 71.3 | 60.0 | 60.0 | 55.0 |
| Polyacrylate Adhesive (DURO-TAK ® 87-2287) | 0.0 | 5.0 | 5.0 | 5.0 |
| Polyacrylate Adhesive (Gelva ® 737) | 5.0 | 0.0 | 0.0 | 0.0 |
| Ethyl Cellulose (Ethocel ® 10) | 0.0 | 5.0 | 0.0 | 5.0 |
| Cellulose Acetate Butyrate (CAB-381-0.5) | 0.0 | 0.0 | 5.0 | 5.0 |
| Polyvinylpyrrolidone (KOLLIDON ® 30) | 10.0 | 10.0 | 10.0 | 10.0 |
| Oleic Acid | 6.0 | 0.0 | 0.0 | 0.0 |
| Dipropylene Glycol | 4.0 | 9.0 | 9.0 | 9.0 |
| Oleyl Alcohol | 0.0 | 6.0 | 6.0 | 6.0 |
| Estradiol | 0.7 | 1.0 | 1.0 | 1.0 |
| Norethindrone Acetate | 3.0 | 4.0 | 4.0 | 4.0 |

Other specific drugs for which the invention can be particularly usefully employed include:

1. α-Adrenergic agonists such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine and Xylometazoline.

2. β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenal, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol and Xamoterol.

3. α-Adrenergic blockers such as Amosulalol, Arotinolol, Dapiprazole, Doxazosin, Ergoloid Mesylates, Fenspiride, Indoramin, Labetalol, Nicergoline, Prazosin, Terazosin, Tolazoline, Trimazosin and Yohimbine.

4. β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Befetolol, Bufuralol, Bunitrolol, Bupranolol, Butidrine Hydrochloride, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranalol, Metoprolol, Moprolol, Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol and Xibenolol.

5. Alcohol deterrents such as Calcium Cyanamide Citrated, Disulfiram, Nadide and Nitrefazole.

6. Aldose reductase inhibitors such as Epalrestat, Ponalrestat, Sorbinil and Tolrestat.

7. Anabolics such as Androisoxazole, Androstenediol, Bolandiol, Bolasterone, Clostebol, Ethylestrenol. Formyldienolone, 4-Hydroxy-19-nortestosterone, Methandriol, Methenolone, Methyltrienolone, Nandrolone, Nandrolone Decanoate, Nandrolone p-Hexyloxyphenylpropionate, Nandrolone Phenpropionate, Norbolethone, Oxymesterone, Pizotyline, Quinbolone, Stenbolone and Trenbolone.

8. Analgesics (dental) such as Chlorobutanol, Clove and Eugenol.

9. Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydrocodone Bitartrate, Hydromorphone, Hydroxypethidine, Isomethadone, Ketobemidone, Levorphanol, Lofentanil, Meperidine, Meptazinol, Metazocine, Methadone Hydrochloride, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papaveretum, Pentazocine, Phenadoxone, Phenazocine, Pheoperidine, Piminodine, Piritramide, Proheptazine, Promedol, Properidine, Propiram, Propoxyphene, Sufentanil and Tilidine.

10. Analgesics (non-narcotic) such as Acetaminophen, Acetaminosalol, Acetanilide, Acetylsalicylsalicylic Acid, Alclofenac, Alminoprofen, Aloxiprin, Aluminum Bis (acetylsalicylate), Aminochlorthenoxazin, 2-Amino-4-picoline, Aminopropylon, Aminopyrine, Ammonium Salicylate, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum Acetylsalicylate, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine Hydrochloride, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalte, Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin and Zomepirac.

11. Anesthetics such as Acetamidoeugenol, Alfadolone Acetate, Alfaxalone, Amucaine, Amolanone, Amylocaine Hydrochloride, Benoxinate, Benzocaine, Betoxycaine, Biphenamine, Bupivacaine, Butacaine, Butaben, Butanilicaine, Burethamine, Buthalital Sodium, Butoxycaine, Carticaine, 2-Chloroprocaine Hydrochloride, Cocaethylene, Cocaine, Cyclomethycaine, Dibucaine Hydrochloride, Dimethisoquin, Dimethocaine, Diperadon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine, Piridocaine, Polidocanol, Pramoxine, Prilocaine, Procaine, Propanidid, Propanocaine, Proparacaine, Propipocaine, Propofol, Propoxycaine Hydrochloride, Pseudococaine, Pyrrocaine, Quinine Urea Hydochloride, Risocaine, Salicyl Alcohol, Tetracaine Hydrochloride, Thialbarbital, Thimylal, Thiobutabarbital, Thiopental Sodium, Tolycaine, Trimecaine and Zolamine.

12. Anorexics such as Aminorex, Amphecloral, Amphetamine, Benzaphetamine, Chlorphentermine, Clobenzorex, Cloforex, Clortermine, Cyclexedrine, Destroamphetamine Sulfate, Diethylpropion, Diphemethoxidine, N-Ethylamphetamine, Fenbutrazate, Fenfluramine, Fenproporex, Furfurylmethylamphetamine, Levophacetoperate, Mazindol, Mefenorex, Metamfeproamone, Methamphetamine, Norpseudoephedrine, Phendimetrazine, Phendimetrazine Tartrate, Phenmetrazine, Phenpentermine, Phenylpropanolamine Hydrochloride and Picilorex.

13. Anthelmintics (Cestodes) such as Arecoline, Aspidin, Aspidinol, Dichlorophen(e), Embelin, Kosin, Napthalene, Niclosamide, Pellertierine, Pellertierine Tannate and Quinacrine.

14. Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Papain, Piperazine, Piperazine Adipate, Piperazine Citrate, Piperazine Edetate Calcium, Piperazine Tartrate, Pyrantel, Pyrvinium Pamoate, á-Santonin, Stilbazium Iodide, Tetrachloroethylene, Tetramisole, thiabendazole, Thymol, Thymyl N-Isoamylcarbamate, Triclofenol Piperazine and Urea Stibamine.

15. Anthelmintics (Onchocerca) such as Ivermectin and Suramin Sodium.

16. Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, Oxamniquine, Praziquantel, Stibocaptate, Stibophen and Urea Stibamine.

17. Anthelmintic (Trematodes) such as Anthiolimine and Tetrachloroethylene.

18. Antiacne drugs such as Adapelene, Algestone Acetophenide, Azelaic Acid, Benzoyl Peroxide, Cyoctol, Cyproterone, Motretinide, Resorcinol, Retinoic Acid, Tetroquinone and Tretinonine.

19. Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox and Urushiol.

20. Antiamebics such as Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Tetracycline, Thiocarbamizine, Thiocarbarsone and Tinidazole.

21. Antiandrogens such as Bifluranol, Cyoctol, Cyproterone, Delmadinone Acetate, Flutimide, Nilutamide and Oxendolone.

22. Antianginals such as Acebutolol, Alprenolol, Amiodarone, Amlodipine, Arotinolol, Atenolol, Bepridil, Bevantolol, Bucumolol, Bufetolol, Bufuralol, Bunitrolol, Bupranolol, Carozolol, Carteolol, Carvedilol, Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotalol, Terodiline, Timolol, Toliprolol and Verapamil.

23. Antiarrhythmics such as Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Encainide, Esmolol, Flecainide, Gallopamil, Hydroquinidine, Indecainide, Indenolol, Ipratropium Bromide, Lidocaine, Lorajmine, Lorcainide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol, Propafenone, Propranolol, Pyrinoline, Quinidine Sulfate, Quinidine, Sotalol, Talinolol, Timolol, Tocainide, Verapamil, Viquidil and Xibenolol.

24. Antiarteriosclerotics such as Pyridinol Carbamate.

25. Antiarthritic/Antirheumatics such as Allocupreide Sodium, Auranofin, Aurothioglucose, Aurothioglycanide, Azathioprine, Calcium 3-Aurothio-2-propanol-1-sulfonate, Celecoxib, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myoral and Penicillamine.

26. Antibacterial (antibiotic) drugs including:

Aminoglycosides such as Amikacin, Apramycin, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols such as Azidamfenicol, Chloramphenicol, Chloramphenicol Palmitate, Chloramphenicol Pantothenate, Florfenicol and Thiamphenicol;

Ansamycins such as Rifamide, Rifampin, Rifamycin and Rifaximin;

β-Lactams, including:
        Carbapenems such as Imipenem;
        Cephalosporins such as Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;
        Cephamycins such as Cefbuperazone, Cefmetazole, Cefminox, Cefetan and Cefoxitin;
        Monobactams such as Aztreonam, Carumonam and Tigemonam;
        Oxacephems such as Flomoxef and Moxolactam;
        Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin O, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin.

27. Antibacterial drugs (synthetic), including:

2,4-Diaminopyrimidines such as Brodimoprim, Tetroxoprim and Trimethoprim;

Nitrofurans such as Furaltadone, Furazolium Chloride, Nifuradene, Nifuratel, Nifurfoline, Nifurpirinol, Nifurprazine, Nifurtoinol and Nitrofurantoin;

Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$Formylsulfisomidine, $N^2$-â-D-Glucosylsulfanilamide, Mafenide, 4'-(Methylsulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine. Sulfamoxole, Sulfanilamide, Sulfanilamidomethanesulfonic Acid Triethanolamine Salt, 4-Sulfanilamidosalicylic Acid, $N^4$-Sulfanilylsulfanilamide, Sulfanilylurea, N-Sulfanilyl-3, 4-xylamide, Sulfanitran, Sulfaperine, Sulfaphenazole. Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N.N' digalactoside, Sulfoxone Sodium and Thiazolsulfone; and others such as Clofoctol, Hexedine, Methenamine, Methenamine Anhydromethylenecitrate, Methenamine Hippurate, Methenamine Mandelate, Methenamine Sulfosalicylate, Nitroxoline and Xibornol. Anticholinergics such as Adiphenine Hydrochloride, Alverine, Ambutonomium Bromide, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium Bromide, Benztropine Mesylate, Bevonium Methyl Sulfate, Biperiden, Butropium Bromide, N-Butylscopolammonium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide, Dibutoline Sulfate, Dicyclomine Hydrochloride, Diethazine, Difemerine, Dihexyverine, Diphemanil Methylsulfate, N-(1,2-Diphenylethyl) nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Chloride, Oxyphencyclimine, Oxyphenonium Bromide, Pentapiperide, Penthienate Bromide, Phencarbamide, Phenglutarimide, Pipenzolate Bromide, Piperidolate, Piperilate, Poldine Methysulfate, Pridinol, Prifinium Bromide, Procyclidine, Propantheline Bromide, Propenzolate, Propyromazine, Scopolamine, Scopolamine N-Oxide, Stilonium Iodide, Stramonium, Sultroponium, Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenytropium Bromide.

28. Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone, Garbapentin, 5-Hydroxytryptophan, Lamotrigine, Lomactil, Magnesium Bromide, Magnesium Sulfate, Mephenytoin, Mephobarbital, Metharbital, Methetoin, Methsuximide, 5-Methyl-5-(3-phenanthryl)hydantoin, 3-Methyl-5-phenylhydantoin, Narcobarbital, Nimetazepam, Nitrazepam, Paramethadione, Phenacemide, Phenetharbital, Pheneturide, Phenobarbital, Phenobarbital Sodium, Phensuximide, Phenylmethylbarbituric Acid, Phenytoin, Phethenylate Sodium, Potassium Bromide, Pregabatin, Primidone, Progabide, Sodium Bromide, Sodium Valproate, Solanum, Strontium Bromide, Suclofenide, Sulthiame, Tetrantoin, Tiagabine, Trimethadione, Valproic Acid, Valpromide, Vigabatrin and Zonisamide.

29. Antidepressants, including:

Bicyclics such as Binedaline, Caroxazone, Citalopram, Dimethazan, Indalpine, Fencamine, Indeloxazine Hydrochcloride, Nefopam, Nomifensine, Oxitriptan, Oxypertine, Paroxetine, Sertraline, Thiazesim, Trazodone, Venlafaxine and Zometapine;

Hydrazides/Hydrazines such as Benmoxine, Iproclozide, Iproniazid, Isocarboxazid, Nialamide, Octamoxin and Phenelzine;

Pyrrolidones such as Cotinine, Rolicyprine and Rolipram;

Tetracyclics such as Maprotiline, Metralindole, Mianserin and Oxaprotiline.

Tricyclics such as Adinazolam, Amitriptyline, Amitriptylinoxide, Amoxapine, Butriptyline, Clomipramine, Demexiptiline, Desipramine, Dibenzepin, Dimetracrine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine and Trimipramine; and others such as Adrafinil, Benactyzine, Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Fluvoxamine Maleate, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine.

30. Antidiabetics, including:

Biguanides such as Buformin, Metformin and Phenformin;

Hormones such as Glucagon and Insulin;

Sulfonylurea derivatives such as Acetohexamide, 1-Butyl-3-metanilylurea, Carbutamide, Chlorpropamide, Glibornuride, Gliclazide, Glipizide, Gliquidone, Glisoxepid, Glyburide, Glybuthiazol(e), Glybuzole, Glyhexamide, Glymidine, Glypinamide, Phenbutamide, Tolazamide, Tolbutamide and Tolcyclamide; and others such as Acarbose, Calcium Mesoxalate and Miglitol.

31. Antidiarrheal drugs such as Acetyltannic Acid, Albumin Tannate, Alkofanone, Aluminum Salicylates—Basic, Catechin, Difenoxin, Diphenoxylate, Lidamidine, Lomotil, Loperamide, Mebiquine, Trillium and Uzarin.
32. Antidiuretics such as Desmopressin, Felypressin, Lypressin, Ornipressin, Oxycinchophen, Pituitary—Posterior, Terlipressin and Vasopressin.
33. Antiestrogens such as Delmadinone Acetate, Ethamoxytriphetol, Tamoxifen and Toremifene.
34. Antifungal drugs (antibiotics), including:
    Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and
    others such as Azaserine, Griseofulvin, Oligomycins, Neomycin Undecylenate, Pyrrolnitrin, Siccanin, Tubercidin and Viridin.
35. Antifungal drugs (synthetic), including:
    Allylamines such as Naftifine and Terbinafine;
    Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole;
    Triazoles such as Fluconazole, Itraconazole and Terconazole; and
    others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate.
36. Antiglaucoma drugs such as Acetazolamide, Befunolol, Betaxolol, Bupranolol, Carteolol, Dapiprazoke, Dichlorphenamide, Dipivefrin, Epinephrine, Levobunolol, Methazolamide, Metipranolol, Pilocarpine, Pindolol and Timolol.
37. Antigonadotropins such as Danazol, Gestrinone and Paroxypropione.
38. Antigout drugs such as Allopurinol, Carprofen, Colchicine, Probenecid and Sulfinpyrazone.
39. Antihistamines, including:
    Alkylamine derivatives such as Acrivastine, Bamipine, Brompheniramine, Chlorpheniramine, Dimethindene, Metron S, Pheniramine, Pyrrobutamine, Thenaldine, Tolpropamine and Triprolidine;
    Aminoalkyl ethers such as Bietanautine, Bromodiphenhydramine, Carbinoxamine, Clemastine, Diphenlypyraline, Doxylamine, Embrammine, Medrylamine, Mephenphydramine, p-Methyldiphenhydramine, Orphenadrine, Phenyltoloxamine, Piprinhydrinate and Setasine;
    Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine;
    Piperazines such as Cetirizine, Chlorcyclizine, Cinnarizine, Clocinizine and Hydroxyzine;
    Tricyclics, including:
        Phenothiazines such as Ahistan, Etymemazine, Fenethazine, N-Hydroxyethylpromethazine Chloride, Isopromethazine, Mequitazine, Promethazine, Pyrathiazine and Thiazinamium Methyl Sulfate; and
    others such as Azatadine, Clobenzepam, Cyproheptadine, Deptropine, Isothipendyl, Loratadine and Prothipendyl; and
    other antihistamines such as Antazoline, Astemizole, Azelastine, Cetoxime, Clemizole, Clobenztropine, Diphenazoline, Diphenhydramine, Fluticasone Propionate, Mebhydroline, Phenindamine, Terfenadine and Tritoqualine.
40. Antihyperlipoproteinemics, including:
    Aryloxyalkanoic acid derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate and Theofibrate;
    Bile acid sequesterants such as Cholestyramine Resin, Colestipol and Polidexide;
    HMG CoA reductase inhibitors such as Fluvastatin, Lovastatin, Pravastatin Sodium and Simvastatin;
    Nicotinic acid derivatives Aluminum Nicotinate, Acipimox, Niceritrol, Nicoclonate, Nicomol and Oxiniacic Acid;
    Thyroid hormones and analogs such as Etiroxate, Thyropropic Acid and Thyroxine; and
    others such as Acifran, Azacosterol, Benfluorex, â-Benzalbutyramide, Carnitine, Chondroitin Sulfate, Clomestone, Detaxtran, Dextran Sulfate Sodium, 5,8,11,14,17-Eicosapentaenoic Acid, Eritadenine, Furazbol, Meglutol, Melinamide, Mytatrienediol, Ornithine, á-Oryzanol, Pantethine, Penataerythritol Tetraacetate, á-Phenylbutyramide, Pirozadil, Probucol, á-Sitosterol, Sultosilic Acid, Piperazine Salt, Tiadenol, Triparanol and Xenbucin.
41. Antihypertensive drugs, including:
    Arylethanolamine derivatives such as Amosulalol, Bufuralol, Dilevalol, Labetalol, Pronethalol, Sotalol and Sulfinalol;
    Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Cartezolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tetraolol, Timolol and Toliprolol;
    Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide and Trichlormethiazide;
    N-Carboxyalkyl (peptide/lactam) derivatives such as Alacepril, Captopril, Cilazapril, Delapril, Enalapril, Enalaprilat, Fosinopril, Lisinopril, Moveltipril, Perindopril, Quinapril and Ramipril;
    Dihydropyridine derivatives such as Amlodipine, Felodipine, Isradipine, Nicardipine, Nifedipine, Nilvadipine, Nisoldipine and Nitrendipine;
    Guanidine derivatives such as Bethanidine, Debrisoquin, Guanabenz, Guanacline, Guanadrel, Guanazodine, Guanethidine, Guanfacine, Guanochlor, Guanoxabenz and Guanoxan;

Hydrazines and phthalazines such as Budralazine, Cadralazine, Dihydralazine, Endralazine, Hydracarbazine, Hydralazine, Pheniprazine, Pildralazine and Todralazine;

Imidazole derivatives such as Clonidine, Lofexidine, Phentolamine, Phentolamine Mesylate, Tiamenidine and Tolonidine;

Quaternary ammonium compounds Azamethonium Bromide, Chlorisondamine Chloride, Hexamethonium, Pentacynium Bis(methyl sulfate), Pentamethonium Bromide, Pentolinium Tartate, Phenactopinium Chloride and Trimethidiunum Methosulfate;

Quinazoline derivatives such as Alfuzosin, Bunazosin, Doxazosin, Prasosin, Terazosin and Trimazosin;

Reserpine derivatives such as Bietaserpine, Deserpidine, Rescinnamine, Reserpine and Syrosingopine;

Sulfonamide derivatives such as Ambuside, Clopamide, Furosemide, Indapamide, Quinethazone, Tripamide and Xipamide; and others such as Ajmaline, à-Aminobutyric Acid, Bufeniode, Candesartan, Chlorthalidone, Cicletaine, Ciclosidomine, Cryptenamine Tannates, Eprosartan, Fenoldopam, Flosequinan, Indoramin, Irbesartan, Ketanserin, Losartan, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Protoveratrines, Raubasine, Rescimetol, Rilmenidene, Saralasin, Sodium Nitroprusside, Ticrynafen, Trimethaphan Camsylate, Tyrosinase, Urapidil and Valsartan.

42. Antihyperthyroids such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, Propylthiouracil, Sodium Perchlorate, Thibenzazoline, Thiobarbital and 2-Thiouracil.

43. Antihypotensive drugs such as Amezinium Methyl Sulfate, Angiotensin Amide, Dimetofrine, Dopamine, Etifelmin, Etilefrin, Gepefrine, Metaraminol, Midodrine, Norepinephrine, Pholedrinead and Synephrine.

44. Antihypothyroid drugs such as Levothyroxine Sodium, Liothyronine, Thyroid, Thyroidin, Thyroxine, Tiratricol and TSH.

45. Anti-Inflammatory (non-steroidal) drugs, including:

Aminoarylcarboxylic acid derivatives such as Enfenamic Acid, Etofenamate, Flufenamic Acid, Isonixin, Meclofenamic Acid, Mefanamic Acid, Niflumic Acid, Talniflumate, Terofenamate and Tolfenamic Acid;

Arylacetic acid derivatives such as Acemetacin, Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac;

Arylbutyric acid derivatives such as Bumadizon, Butibufen, Fenbufen and Xenbucin;

Arylcarboxylic acids such as Clidanac, Ketorolac and Tinoridine;

Arylpropionic acid derivatives such as Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid, Suprofen and Tiaprofenic Acid;

Pyrazoles such as Difenamizole and Epirizole;

Pyrazolones such as Apazone, Benzpiperylon, Feprazone, Mofebutazone, Morazone, Oxyphenbutazone, Phenybutazone, Pipebuzone, Propyphenazone, Ramifenazone, Suxibuzone and Thiazolinobutazone;

Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Naphthyl Salicylate, Olsalazine, Parsalmide, Phenyl Acetylsalicylate, Phenyl Salicylate, Salacetamide, Salicylamine O-Acetic Acid, Salicylsulfuric Acid, Salsalate and Sulfasalazine;

Thiazinecarboxamides such as Droxicam, Isoxicam, Piroxicam and Tenoxicam; and others such as å-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap.

46. Antimalarial drugs such as Acedapsone, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid, Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Diabasic.

47. Antimigraine drugs such as Alpiropride, Dihydroergotamine, Eletriptan, Ergocornine, Ergocorninine, Ergocryptine, Ergot, Ergotamine, Flumedroxone acetate, Fonazine, Lisuride, Methysergid(e), Naratriptan, Oxetorone, Pizotyline, Rizatriptan and Sumatriptan.

48. Antinauseant drugs such as Acetylleucine Monoethanolamine, Alizapride, Benzquinamide, Bietanautine, Bromopride, Buclizine, Chlorpromazine, Clebopride, Cyclizine, Dimenhydrinate, Dipheniodol, Domperidone, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine and Trimethobenzamide.

49. Antineoplastic drugs, including:

Alkylating agents, including:

Alkyl sulfonates such as Busulfan, Improsulfan and Piposulfan;

Aziridines such as Benzodepa, Carboquone, Meturedepa and Uredepa;

Ethylenimines and methylmelamines such as Altretamine, Sulfosamide, Triethylenemelamine, Triethylenephosphoramide, Triethylenethiophosphoramide and Trimethylolomelamine;

Nitrogen mustards such as Chlorambucil, Chlornaphazine, Chclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard;

Nitrosoureas such as Carmustine, Chlorozotocin, Fotemustine, Lomustine, Nimustine and Ranimustine; and others such as Camptothecin, Dacarbazine, Mannomustine, Mitobronitol, Mitolactol and Pipobroman;

Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Rufocromomycin, Streptonigrin, Streptozocin, Tubercidin, Ubenimex, Zinostatin and Zorubicin;

Antimetabolites, including:
  Folic acid analogs such as Denopterin, Methotrexate, Pteropterin and Trimetrexate;
  Purine analogs such as Fludarabine, 6-Mercaptopurine, Thiamiprine and Thioguanaine; and
  Pyrimidine analogs such as Ancitabine, Azacitidine, 6-Azauridine, Carmofur, Cytarabine, Doxifluridine, Enocitabine, Floxuridine, Fluroouracil and Tegafur;

Enzymes such as L-Asparaginase; and others such as Aceglatone, Amsacrine, Bestrabucil, Bisantrene, Bryostatin 1, Carboplatin, Cisplatin, Defofamide, Demecolcine, Diaziquone, Dolastatins, Elfornithine, Elliptinium Acetate, Etoglucid, Etoposide, Gallium Nitrate, Hydroxyurea, Interferon-á, Interferon-â, Interferon-ã, Interleukine-2, Lentinan, Letrozole, Lonidamine, Mitoguazone, Mitoxantrone, Mopidamol, Nitracrine, Pentostatin, Phenamet, Pirarubicin, Podophyllinicc Acid, 2-Ethythydrazide, Polynitrocubanes, Procarbazine, PSK7, Razoxane, Sizofiran, Spirogermanium, Symplostatin 1, Taxol, Teniposide, Tenuazonic Acid, Triaziquone, 2.2'.2"-Trichlorotriethylamine, Urethan, Vinblastine, Vincristine, Vindesine and Vinorelbine.

50. Antineoplastic (hormonal) drugs, including:
  Androgens such as Calusterone, Dromostanolone Propionate, Epitiostanol, Mepitiostane and Testolactone;
  Antiadrenals such as Aminoglutethimide, Mitotane and Trilostane;
  Antiandrogens such as Flutamide and Nilutamide; and
  Antiestrogens such as Tamoxifen and Toremifene.

51. Antineoplastic adjuncts including folic acid replenishers such as Frolinic Acid.

52. Antiparkinsonian drugs such as Amantadine, Apomorphine, Benserazide, Bietanautine, Biperiden, Bromocriptine, Budipine, Cabergoline, Carbidopa, Deprenyl (a/k/a L-deprenyl, L-deprenil, L-deprenaline and selegiline), Dexetimide, Diethazine, Diphenhydramine, Droxidopa, Ethopropazine, Ethylbenzhydramine, Levodopa, Naxagolide, Pergolide, Piroheptine, Pramipexole, Pridinol, Prodipine, Quinpirole, Remacemide, Ropinirole, Terguride, Tigloidine and Trihexyphenidyl Hydrochloride.

53. Antipheochromocytoma drugs such as Metyrosine, Phenoxybenzamine and Phentolamine.

54. Antipneumocystis drugs such as Effornithine, Pentamidine and Sulfamethoxazole.

55. Antiprostatic hypertrophy drugs such as Gestonorone Caproate, Mepartricin, Oxendolone and Proscar7.

56. Antiprotozoal drugs (Leshmania) such as Antimony Sodium Gluconate, Ethylstibamine, Hydroxystilbamidine, N-Methylglucamine, Pentamidine, Stilbamidine and Urea Stibamine.

57. Antiprotozoal drugs (Trichomonas) such as Acetarsone, Aminitrozole, Anisomycin, Azanidazole, Forminitrazole, Furazolidone, Hachimycin, Lauroguadine, Mepartricin, Metronidazole, Nifuratel, Nifuroxime, Nimorazole, Secnidazole, Silver Picrate, Tenonitrozole and Tinidazole.

58. Antiprotozoal drugs (Trypanosma) such as Benznidazole, Eflornithine, Melarsoprol, Nifurtimox, Oxophenarsine, Hydrochloride, Pentamidine, Propamidine, Puromycin, Quinapyramine, Stilbamidine, Suramin Sodium, Trypan Red and Tryparasmide.

59. Antipuritics such as Camphor, Cyproheptadine, Dichlorisone, Glycine, Halometasone, 3-Hydroxycamphor, Menthol, Mesulphen, Methdilazine, Phenol, Polidocanol, Risocaine, Spirit of Camphor, Thenaldine, Tolpropamine and Trimeprazine.

60. Antipsoriatic drugs such as Acitretin, Ammonium Salicylate, Anthralin, 6-Azauridine, Bergapten(e), Chrysarobin, Etretinate and Pyrogallol.

61. Antipsychotic drugs, including:
  Butyrophenones such as Benperidol, Bromperidol, Droperidol, Fluanisone, Haloperidol, Melperone, Moperone, Pipamperone, Sniperone, Timiperone and Trifluperidol;
  Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine;
  Thioxanthenes such as Chlorprothixene, Clopenthixol, Flupentixol and Thiothixene;
  other tricyclics such as Benzquinamide, Carpipramine, Clocapramine, Clomacran, Clothiapine, Clozapine, Opipramol, Prothipendyl, Tetrabenazine, and Zotepine; and
  others such as Alizapride, Amisulpride, Buramate, Fluspirilene, Molindone, Penfluridol, Pimozide, Spirilene and Sulpiride.

62. Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Bufexamac, Bumadizon, Calcium Acetysalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 5'-Nitro-2'-propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide O-Acetic Acid, Sodium Salicylate, Sulfamipyrine, Tetrandrine and Tinoridine.

63. Antirickettsial drugs such as p-Aminobenzoic Acid, Chloramphenicol, Chloramphenicol Palmitate, Chloramphenicol Pantothenate and Tetracycline.

64. Antiseborrheic drugs such as Chloroxine, 3-O-Lauroylpyridoxol Diacetate, Pioctone, Pyrithione, Resorcinol, Selenium Sulfides and Tioxolone.

65. Antiseptics, including:

Guanidines such as Alexidine, Ambazone, Chlorhexidine and Picloxydine;

Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Flurosalan, Iodic Acid, Iodine, Iodine Monochloride, Iodine Trichloride, Iodoform, Methenamine Tetraiodine, oxychlorosene, Povidone-Iodine, Sodium Hypochlorite, Sodium Iodate, Symclosene, Thymol Iodide, Triclocarban, Triclosan and Troclosene Potassium;

Mercurial compounds such as Hydragaphen, Meralein Sodium, Merbromin, Mercuric Chloride, Mercuric Chloride, Ammoniated, Mercuric Sodium p-Phenolsulfonate, Mercuric Succinimide, Mercuric Sulfide, Red, Mercurophen, Mercurous Acetate, Mercurous Chloride, Mercurous Iodide, Nitromersol, Potassium Tetraiodomercurate(II), Potassium Triiodomercurate(II) Solution, Thimerfonate Sodium and Thimerosal;

Nitrofurans such as Furazolidone, 2-(Methoxymethyl)-5-nitrofuran, Nidroxyzone, Nifuroxime, Nifurzide and Nitrofurazone;

Phenols such as Acetomeroctol, Bithionol, Cadmium Salicylate, Carvacrol, Chloroxylenol, Clorophene, Cresote, Cresol(s), p-Cresol, Fenticlor, Hexachlorophene, 1-Napthyl Salicylate, 2-Napthyl Salicylate, 2,4,6-Tribromo-m-cresol, and 3', 4',5-Trichlorosalicylanilide;

Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxquinoline, 8-Hydroxquinoline Sulfate and Iodochlorhydroxyquin; and others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatol7, Noxytiolin, Ornidazole, â-Propiolactone, â-Terpineol.

66. Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, Pipoxolan Hydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-lTrimethyl-3,3-diphenyl-propylamine, Tropenzile, Trospium Chloride and Xenytropium Bromide.

67. Antithrombotic drugs such as Anagrelide, Argatroban, Cilostazol, Chrysoptin, Daltroban, Defibrotide, Enoxaparin, Fraxiparine7, Indobufen, Lamoparan, Ozagrel, Picotamide, Plafibride, Reviparin, Tedelparin, Ticlopidine, Triflusal and Warfarin.

68. Antitussive drugs such as Allocamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, a,a-Diphenyl-2-piperidinepropanol, Dropropizine, Drotebanol, Eprazinone, Ethyl Dibunate, Ethylmorphine, Fominoben, Guiaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol.

69. Antiulcerative drugs such as Aceglutamide Aluminum Complex, å-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostol, Nizatidine, Omeprazole, Ornoprostil, â-Oryzanol, Pifarnine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Thrithiozine, Troxipide and Zolimidine.

70. Antiurolithic drugs such as Acetohydroxamic Acid, Allopurinol, Potassium Citrate and Succinimide.

71. Antivenin drugs such as Lyovac7 Antivenin.

72. Antiviral drugs, including:

Purines and pyrimidinones such as Acyclovir, Cytarabine, Dideoxyadenosine, Dideoxycytidine, Dideoxyinosine, Edoxudine, Floxuridine, Ganciclovir, Idoxuridine, Inosine Pranobex, MADU, Penciclovir, Trifluridine, Vidrarbine and Zidovudiine; and others such as Acetylleucine Monoethanolamine, Amantadine, Amidinomycin, Cosalane, Cuminaldehyde Thiosemicarbzone, Foscarnet Sodium, Imiquimod, Interferon-á, Interferon-â, Interferon-ã, Kethoxal, Lysozyme, Methisazone, Moroxydine, Podophyllotoxin, Ribavirin, Rimantadine, Stallimycin, Statolon, Tromantadine and Xenazoic Acid.

73. Anxiolytic drugs, including:

Arylpiperazines such as Buspirone, Gepirone, Isapirone and Tondospirone.

Benzodiazepine derivatives such as Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam;

Carbamates such as Cyclarbamate, Emylcamate, Hydroxyphenamate, Meprobamate, Phenprobamate and Tybamate; and others such as Alpidem, Benzoctamine, Captodiamine, Chlormezanone, Etifoxine, Flesinoxan, Fluoresone, Glutamic Acid, Hydroxyzine, Lesopitron, Mecloralurea, Mephenoxalone, Mirtazepine, Oxanamide, Phenaglycodol, Suriclone and Zatosetron.

74. Benzodiazepine antagonists such as Flumazenil.
75. Bronchodilators, including:

Ephedrine derivatives such as Albuterol, Bambuterol, Bitolterol, Carbuterol, Clenbuterol, Clorprenaline, Dioxethedrine, Ephedrine, Epiniphrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Salmeterol, Soterenol, Terbutaline and Tulobuterol;

Quaternary ammonium compounds such as Bevonium Methyl Sulfate, Clutropium Bromide, Ipratropium Bromide and Oxitropium Bromide;

Xanthine derivatives such as Acefylline, Acefylline Piperazine, Ambuphylline, Aminophylline, Bamifylline, choline Theophyllinate, Doxofylline, Dyphylline, Enprofylline, Etamiphyllin, Etofylline, Guaithylline, Proxyphylline, Theobromine, 1-Theobromineacetic Acid and Theophylline; and others such as Fenspiride, Medibazine, Montekulast, Methoxyphenanime, Tretoquinol and Zafirkulast.

76. Calcium channel blockers, including:

Arylalkylamines such as Bepridil, Ditiazem, Fendiline, Gallopanil, Prenylamine, Terodiline and Verapamil;

Dihydropyridine derivatives such as Felodipine, Isradipine, Nicardipine, Nifedipine, Nilvadipine, Nimodipine, Nisoldipine and Nitrendipine;

Piperazine derivatives such as Cinnarizine, Flunarisine and Lidoflazine; and others such as Bencyclane, Etafenone and Perhexiline.

77. Calcium regulators such as Calcifediol, Calcitonin, Calcitriol, Clodronic Acid, Dihydrotachysterol, Elcatonin, Etidronic Acid, Ipriflavone, Pamidronic Acid, Parathyroid Hormone and Teriparatide Acetate.
78. Cardiotonics such as Acefylline, Acetyldigititoxins, 2-Amino-4-picoline, Amrinone, Benfurodil Hemisuccinate, Buclasdesine, Cerberoside, Camphotamide, Convallatoxin, Cymarin, Denopamine, Deslanoside, Ditalin, Digitalis, Digitoxin, Digoxin, Dobutamine, Dopamine, Dopexamine, Enoximone, Erythrophleine, Fenalcomine, Gitalin, Gitoxin, Glycocyamine, Heptaminol, Hydrastinine, Ibopamine, Lanotodises, Metamivam, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol.
79. Chelating agents such as Deferozmine, Ditiocarb Sodium, Edetate Calcium Disodium, Edetate Disodium, Edeate Sodium, Edetate Trisodium, Penicillamine, Pentetate Calcium Trisodium, Pentectic Acid, Succimer and Trientine;
80. Cholecystokinin antagonists such as Proglumide.
81. Cholelitholytic agents such as Chenodiol, Methyl tert-Butyl Ether, Monooctanoin and Ursodiol.
82. Choleretics such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, á-Ethylbenzyl Alcohol, Exiproben, Feguprol, Fencibutirol, Fenipentol, Florantyrone, Hymecromone, Menbutone, 3-(o-Methoxyphenyl)-2-phenylacrylic Acid, Metochalcone, Moquizone, Osalmid, Ox Bile Extract, 4.4'-Oxydi-2-butanol, Piprozolin, Prozapine, 4-Salicyloylmorpholine, Sincalide, Taurocholic Acid, Timonacic, Tocamphyl, Trepibutone and Vanitiolide.
83. Cholinergic agents such as Aceclidine, Acetylcholine Bromide, Acetylcholide Chloride, Aclatonium Napadisilate, Benzpyrinium Bromide, Bethanechol chloride, Carbachol, Carpronium chloride, Demecarium Bromide, Dexpanthenol, Diisopropyl Paraoxon, Echothiophate Iodide, Edrophomium chloride, Eseridine, Furtrethonium, Isoflurophate, Methacholine chloride, Muscarine, Neostigmine, Oxapropanium Iodide, Physostigmine and Pyridostigmine Bromide.
84. Cholinesterase inhibitors such as Ambenonium Chloride, Distigmine Bromide and Galanthamine.
85. Cholinesterase reactivators such as Obidoximine Chloride and Pralidoxime Chloride.
86. Central nervous system stimulants and agents such as Amineptine, Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethylamphetamine, Ethamivan, Etifelmin, Etryptamine, Fencamfamine, Fenethylline, Fenosolone, Flurothyl, Galanthamine, Hexacyclonate Sodium, Homocamfin, Mazindol, Megexamide, Methamphetamine, Methylphenidate, Nikethamide, Pemoline, Pentylenetetrazole, Phenidimetrazine, Phenmetrazine, Phentermine, Picrotoxin, Pipradrol, Prolintane and Pyrovalerone.
87. Decongestants such as Amidephrine, Cafaminol, Cyclopentamine, Ephedrine, Epinephrine, Fenoxazoline, Indanazoline, Metizoline, Naphazoline, Nordefrin Hydrochloride, Octodrine, Oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline.
88. Dental agents, including:

Bisphosphonates (anti-periodontal disease and bone resorption) such as Alendronate, Clodronate, Etidronate, Pamidronate and Tiludronate;

Carries Prophylactics such as Arginine and Sodium Fluoride; Desensitizing Agents such as Potassium Nitrate and Citrate Oxalate.

89. Depigmentors such as Hydroquinine, Hydroquinone and Monobenzone.
90. Diuretics, including:

organomercurials such as Chlormerodrin, Meralluride, Mercamphamide, Mercaptomerin Sodium, Mercumallylic Acid, Mercumatilin Sodium, Mercurous Chloride and Mersalyl;

Pteridines such as Furterene and Triamterene;

Purines such as Acefylline, 7-Morpholinomethyltheophylline, Pamabrom, Protheobromine and Theobromine;

Steroids such as Canrenone, Oleandrin and Spironolactone;

Sulfonamide derivatives such as Acetazolmide, Ambuside, Azosemide, Bumetanide, Butazolamide, Chloraminophenamide, Clofenamide, Clopamide, Clorexolene, Diphenylmethane-4.4'-disulfonamide, Disulfamide, Ethoxzolamide, Furosemide, Indapamide, Mefruside, Methazolamide, Piretanide, Quinethazone, Torsemide, Tripamide and Xipamide;

Uracils such as Aminometradine and Amisometradine;

others such as Amanozine, Amiloride, Arbutin, Chlorazanil, Ethacrynic Acid, Etozolin, Hydracarbazine, Isosorbide, Mannitol, Metochalcone, Muzolimine, Perhexiline, Ticrynafen and Urea.

91. Dopamine receptor agonists such as Bromocriptine, Dopexamine, Fenoldopam, Ibopamine, Lisuride, Naxagolide and Pergolide.
92. Ectoparasiticides such as Amitraz, Benzyl Benzoate, Carbaryl, Crotamiton, DDT, Dixanthogen, Isobornyl Thiocyanoacetate—Technical, Lime Sulfurated Solution, LIndane, Malathion, Mercuric Oleate, Mesulphen and Sulphur—Pharmaceutical.
93. Enzymes, including:

Digestive enzymes such as á-Amylase (Swine Pancreas), Lipase, Pancrelipase, Pepsin and Rennin;

Mucolytic enzymes such as Lysozyme;

Penicillin inactivating enzymes such as Penicillinase; and

Proteolytic enzymes such as Collagenase, Chymopapain, Chymotrypsins, Papain and Trypsin.
94. Enzyme inducers (hepatic) such as Flumecinol.
95. Estrogens (non-steroidal) such as Benzestrol, Broparoestrol, Chlorotrianisene, Dienestrol, Diethylstilbestrol, Diethylstilbestrol Diprorionate, Dimestrol, Fosfestrol, Hexestrol, Methallenestril and Methestrol.
96. Gastric secretion inhibitors such as Enterogastrone and Octreotide.
97. Glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, ydrocortisone Phosphate, Hydrocortisone 21-Sodium Succinate, Hydrocortisone Tebutate, Mazipredone, Medrysone, Meprednisone, Methyolprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide and Triamcinolone Hexacetonide.
98. Gonad-Stimulating principles such as Buserelin, Clomiphene, Cyclofenil, Epimestrol, FSH, HCG and LH-RH.
99. Gonadotropic hormones such as LH and PMSG.
100. Growth hormone inhibitors such as Octreotide and Somatostatin.
101. Growth hormone releasing factors such as Semorelin.
102. Growth stimulants such as Somatotropin.
103. Hemolytic agents such as Phenylhydrazine and Phenylhydrazine Hydrochloride.
104. Heparin antagonists such as Hexadimethrine Bromide and Protamines.
105. Hepatoprotectants such as S-Adenosylmethionine, Betaine, Catechin, Citolone, Malotilate, Orazamide, Phosphorylcholine, Protoporphyrin IX, Silymarin-Group, Thiotic Acid and Tiopronin.
106. Immunomodulators such as Amiprilose, Bucillamine, Ditiocarb Sodium, Inosine Pranobex, Interferon-y, Interleukin-2, Lentinan, Muroctasin, Platonin, Procodazole, Tetramisole, Thymomodulin, Thymopentin and Ubenimex.
107. Immunosuppressants such as Azathioprine, Cyclosporins and Mizoribine.
108. Ion exchange resins such as Carbacrylic Resins, Cholestyramine Resin, Colestipol, Polidexide, Resodec and Sodium Polystyrene Sulfonate.
109. Lactation stimulating hormone such as Prolactin.
110. LH-RH agonists such as Buserelin, Goserelin, Goserelin Acetate, Leuprolide, Nafarelin, and Triptorelin.
111. Lipotropic agents such as N-Acetylmethionine, Choline Chloride, Choline Dehydrocholate, Choline Dihydrogen Citrate, Inositol, Lecithin and Methionine.
112. Lupus erythematosus suppressants such as Bismuth Sodium Triglycollamate, Bismuth Subsalicylate, Chloroquine and Hydroxychloroquine.
113. Mineralcorticoids such as Aldosterone, Deoxycorticosterone, Deoxycorticosterone Acetate and Fludrocortisone.
114. Miotic drugs such as Carbachol, Physostigmine, Pilocarpine and Pilocarpus.
115. Monoamine oxidase inhibitors such as Deprenyl, Iproclozide, Iproniazid, Isocarboxazid, Moclobemide, Octomoxin, Pargyline, Phenelzine, Phenoxypropazine, Pivalylbenzhydrazine, Prodipine, Toloxatone and Tranylcypromine.
116. Mucolytic agents such as Acetylcysteine, Bromhexine, Carbocysteine, Domiodol, Letosteine, Lysozyme, Mecysteine Hydrochloride, Mesna, Sobrerol, Stepronin, Tiopronin and Tyloxapol.
117. Muscle relaxants (skeletal) such as Afloqualone, Alcuronium, Atracurium Besylate, Baclofen, Benzoctamine, Benzoquinonium Chloride, C-Calebassine, Carisoprodol, Chlormezanone, Chlorphenesin Carbamate, Chlorproethazine, Chlozoxazone, Curare, Cyclarbamate, Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Lauexium Methyl Sulfate, Leptodactyline, Memantine, Mephenesin, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam, Thiocolchicoside, Tizanidine, Tolperisone, Tubocurarine Chloride, Vecuronium Bromide and Zoxolamine.
118. Narcotic antagonists such as Amiphenazole, Cyclazocine, Levallorphan, Nadide, Nalmfene, Nalorphine, Nalorphine Dinicotinate, Naloxone and Naltrexone.
119. Neuroprotective agents such as Dizocilpine.

120. Nootropic agents such as Aceglutamide, Acetylcarnitine, Aniracetam, Bifematlane, Exifone, Fipexide, Idebenone, Indeloxazune Hydrochloride, Nizofenone, Oxiracetam, Piracetam, Propentofylline, Pyritinol and Tacrine.
121. Ophthalmic agents such as 15-ketoprostaglandins.
122. Ovarian hormone such as Relaxin.
123. Oxytocic drugs such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2\alpha}$ and Sparteine.
124. Pepsin inhibitors such as Sodium Amylosulfate.
125. Peristaltic stimulants such as Cisapride.
126. Prolactin inhibitors such as Metergoline.
127. Prostaglandins and prostaglandin analogs such as Arbaprostil, Carboprost, Enprostil, Bemeprost, Limaprost, Misoprostol, Ornoprostil, Prostacyclin, Prostaglandin $E_1$, Prostaglandin $E_2$, Prostagland in $F_{2\alpha}$ Rioprostil, Rosaprostol, Sulprostone and Trimoprostil.
128. Protease inhibitors such as Aprotinin, Camostat, Gabexate and Nafamostat.
129. Respiratory stimulants such as Almitrine, Bemegride, Carbon Dioxide, Cropropamide, Crotethamide, Dimefline, Dimorpholamine, Doxapram, Ethamivan, Fominoben, Lobeline, Mepixanox, Metamivam, Nikethamide, Picrotoxin, Pimeclone, Pyridofylline, Sodium Succinate and Tacrine.
130. Sclerosing agents such as Ethanolamine, Ethylamine, 2-Hexyldecanoic Acid, Polidocanol, Quinine Bisulfate, Quinine Urea Hydrochloride, Sodium Ricinoleate, Sodium Tetradecyl Sulfate and Tribenoside.
131. Sedatives and hypnotics, including:
Acyclic ureides such as Acecarbromal, Apronalide, Bomisovalum, Capuride, Carbromal and Ectylurea;
Alcohols such as Chlorhexadol, Ethchlorvynol, Meparfynol, 4-Methyl-5-thiazoleethanol, tert-Pentyl Alcohol and 2,2,2-Trichloroethanol;
Amides such as Butoctamide, Diethylbromoacetamide, Ibrotamide, Isovaleryl Diethylamide, Niaprazine, Tricetamide, Trimetozine, Zolpidem and Zopiclone;
Barbituric acid derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallylpropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium and Vinylbital;
Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temazepam and Triazolam;
Bromides such as Ammonium Bromide, Calcium Bromide, Calcium Bromolactobionate, Lithium Bromide, Magnesium Bromide, Potassium Bromide and Sodium Bromide;
Carbamates such as Amyl Carbamate—Tertiary, Ethinamate, Hexaprpymate, Meparfynol Carbamate, Novonal and Tricholorourethan;
Chloral derivatives such as Carbocloral, Chloral Betaine, Chloral Formamide, Chloral Hydrate, Chloralantipyrine, Dichloralphenazone, Pentaerythritol Chloral and Triclofos;
Piperidinediones such as Glutehimide, Methyprylon, Piperidione, Pyrithyldione, Taglutimide and Thalidomide;
Quinazolone derivatives such as Etaqualone, Mecloqualone and Methaqualone; and
others such as Acetal, Acetophenone, Aldol, Ammonium Valerate, Amphenidone, d-Bornyl á-Bromoisovalerate, d-Bornyl Isovalerate, Bromoform, Calcium 2-Ethylbutanoate, Carfinate, á-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane and Sulfonmethane.
132. Thrombolytic agents such as APSAC, Plasmin, Pro-Urokinase, Streptokinase, Tissue Plasminogen Activator and Urokinase;
133. Thyrotropic hormones such as TRH and TSH.
134. Uricosurics such as Benzbromarone, Ethebenecid, Orotic Acid, Oxycinchophen, Probenecid, Sulfinpyrazone, Ticrynafen and Zoxazolamine.
135. Vasodilators (cerebral) such as Bencyclane, Cinnarizine, Citicoline, Cyclandelate, Ciclonicate, Diisopropylamine Dichloractetate, Eburnamonine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil.
136. Vasodilators (coronary) such as Amotriphene, Bendazol, Benfurodil Hemisuccinate, Benziodarone, Chloacizine, Chromonar, Clobenfurol, Clonitrate, Dilazep, Dipyridamole, Droprenilamine, Efloxate, Erythritol, Erythrityl Tetranitrate, Etafenone, Fendiline, Floredil, Ganglefene, Hexestrol Bis(β-diethylaminoethyl ether), Hexobendine, Itramin Tosylate, Khellin, Lidoflazine, Mannitol Hexanitrate, Medibazine, Nicorandil, Nitroglycerin, Pentaerythritol Tetranitrate, Pentrinitrol, Perhexiline, Pimefylline, Prenylamine, Propatyl Nitrate, Pyridofylline, Trapidil, Tricromyl, Trimetazidine, Trolnitrate Phosphate and Visnadine.
137. Vasodilators (peripheral) such as Aluminum Nicotinate, Bamethan, Bencyclane, Betahistine, Bradykinin, Brovincamine, Bufoniode, Buflomedil, Butalamine, Cetiedil, Ciclonicate, Cinepazide, Cinnarizine, Cyclandelate, Diisopropylamine Dichloracetate, Eledoisin, Fenoxidil, Flunarisine, Heronicate, Ifenprodil, Inositol Niacinate, Isoxsuprine, Kallidin, Kallikrein, Moxisylyte, Nafronyl, Nicametate, Nicergoline, Nicofuranose, Nicotinyl Alcohol, Nylidrin, Pentifylline, Pentoxifylline, Piribedil, Protaglandin $E_1$, Suloctidil and Xanthinal Niacinate.
138. Vasoprotectants such as Benzarone, Bioflavonoids, Chromocarb, Clobeoside, Diosmin, Dobesilate Calcium, Escin, Rolescutol, Leucocyanidin, Metescufylline, Quercetin, Rutin and Troxerutin.
139. Vitamins, vitamin sources, and vitamin extracts such as Vitamins A, B, C, D, E, and K and derivatives thereof, Calciferols, Glycyrrhiza and Mecobalamin.
140. Vulnerary agents such as Acetylcysteine, Allantoin, Asiaticoside, Cadexomer Iodine, Chitin, Dextranomer and Oxaceprol.
141. Anticoagulants such as heparin.
142. Miscellaneous such as Erythropoietin (Hematinic), Filgrastim, Finasteride (Benign Prostate Hypertrophy), Interferon Beta 1—Alpha (Multiple Sclerosis) and Tretinonin (Urinary Incontinence).

The amount of active agent to be incorporated in the carrier composition will vary depending on the particular active agent, the desired therapeutic effect, and the time span for which the transdermal system is to provide therapy. Normally, the amount of active agent in the transdermal system can vary from about 0.1% to about 50%, and preferably from about 0.1% to about 30% by weight based on the dry weight of the total adhesive matrix composition. For lower dose concentrations permitted by this invention, such as with steroids and hormones, the preferred amount is from about 0.1% to about 10%.

While not essential, it is preferred that the androgenic hormones be incorporated near, at or above saturation with respect to its concentration in the adhesive matrix composition.

The term "adhesive matrix composition" as used herein refers to any non-aqueous adhesive material into which an active agent is solubilized or homogeneously blended either without, or in combination or admixture with, other ingredients useful for facilitating transdermal drug delivery, such as crystallization inhibitors, solubility enhancers, permeation enhancers, solvents, co-solvents and other types of additives. An "adhesive" as used herein means any natural or synthetic material that is capable of sticking to the site of topical application. The term "pressure-sensitive adhesive" as used herein refers to an adhesive which adheres instantaneously to most surfaces with the application of very slight pressure and remains permanently tacky. An adhesive is a pressure-sensitive adhesive within the meaning of that term as used herein if it has the properties of an adhesive pressure-sensitive adhesive per se or functions as the same by admixture with tackifiers, plasticizers, cross-linking agents or other additives.

Suitable adhesives include all of the non-toxic natural and synthetic polymers known for or suitable for use in transdermal devices as adhesives including acrylic polymers, gums, silicone-based polymers (broadly referred to as "polysiloxanes") and rubber-based adhesives such as polyisobutylenes, polybutylenes, ethylene/vinyl acetate and vinyl acetate based adhesives, styrene/butadiene adhesives, polyisoprenes, styrenes and styrene block copolymers and block amide copolymers.

Suitable polysiloxanes include silicone pressure-sensitive adhesives which are based on two major components: a polymer, or gum, and a tackifying resin. The polysiloxane adhesive is usually prepared by cross-linking the gum, typically a high molecular weight polydiorganosiloxane, with the resin, to produce a three-dimensional silicate structure, via a condensation reaction in an appropriate organic solvent. The ratio of resin to polymer is the most important factor which can be adjusted in order to modify the physical properties of polysiloxane adhesives. Sobieski, et al., "Silicone Pressure Sensitive Adhesives," *Handbook of Pressure-Sensitive Adhesive Technology*, 2nd ed., pp. 508–517 (D. Satas, ed.), Van Nostrand Reinhold, New York (1989).

Further details and examples of silicone pressure-sensitive adhesives which are useful in the practice of this invention are described in the following U.S. Pat. Nos. 4,591,622; 4,584,355; 4,585,836; and 4,655,767.

Suitable silicone pressure-sensitive adhesives are commercially available and include the silicone adhesives sold under the trademarks BIO-PSA® by Dow Corning Corporation, Medical Products, Midland, Michigan.

In particularly preferred embodiments of the invention, the adhesive matrix composition comprises a pressure-sensitive adhesive, and more preferably a blend of one or more pressure-sensitive acrylic polymers and polysiloxanes.

The term "acrylic polymer" is intended to be used interchangeably with the terms acrylate polymer, polyacrylate and polyacrylic adhesive polymers as used herein and as known in the art.

The acrylic polymers useful in practicing the invention are polymers of one or more monomers of acrylic acids and other copolymerizable monomers. The acrylic polymers also include copolymers of alkyl acrylates and/or methacrylates and/or copolymerizable secondary monomers or monomers with functional groups. By varying the amount of each type of monomer added, the cohesive properties of the resulting acrylic polymer can be changed as is known in the art. In general, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, butyl methacrylate, hexyl acrylate, hexyl methacrylate, 2-ethylbutyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate and other monomers having at least one unsaturated double bond which participates in copolymerization reaction in one molecule and a functional group on its side chain such as a carboxyl group, a hydroxyl group, a sulfoxyl group, an amino group, an amino group and an alkoxyl, as well as a variety of other monmeric units including alkylene, hydroxy-substituted alkylene, carboxylic acid-substituted alkylene, vynylalkanoate, vinylpyrrolidone, vinylpyridine, vinylpirazine, vinylpyrrole, vinylimidazole, vinylcaprolactam, vinyloxazole, vyinlacate, vinylpropionate and vinylmorpholine.

Further details and examples of acrylic adhesives which are suitable in the practice of the invention are described in Satas, "Acrylic Adhesives," *Handbook of Pressure-Sensitive Adhesive Technology*, $2^{nd}$ ed., pp. 396–456 (D. Satas, ed.), Van Nostrand Reinhold, New York (1989).

Suitable acrylic adhesives are commercially available and include the polyacrylate adhesives sold under the trademarks DURO-TAK® by National Starch Company, Bridgewater, N.J.; GELVA® by Solutia, St. Louis, Mo.; HRJ by Schenectady International, Inc., Chicago, Ill.; and EUDRAGIT® by Roehm Pharma GmbH, Darmstadt, Federal Republic of Germany.

The amount of the adhesive to be used depends on the concentration of active agent used to achieve a therapeutic effect. Typically, the adhesive is in an amount of about 5% to about 90%, and preferably about 10% to about 90%, and most preferably about 20% to about 75% by weight based on the dry weight of the total adhesive matrix composition.

The adhesive matrix compositions of the present invention can also contain one or more solvents and/or co-solvents. Such solvents and/or co-solvents are those known in the art, and are non-toxic, pharmaceutically acceptable substances, preferably liquids, which do not substantially negatively affect the adhesive properties of the transdermal system or the solubility of the active agents at the concentrations used. The solvent and/or co-solvent can be for the active agent or for the matrix materials, or both.

Suitable solvents include volatile liquids such as alcohols (e.g., methyl, ethyl, isopropyl alcohols and methylene chloride); ketones (e.g., acetone); aromatic hydrocarbons such as benzene derivatives (e.g., xylenes and toluenes); lower molecular weight alkanes and cycloalkanes (e.g., hexanes, heptanes and cyclohexanes); and alkanoic acid esters (e.g., ethyl acetate, n-propyl acetate, isobutyl acetate, n-butyl acetate isobutyl isobutyrate, hexyl acetate, 2-ethylhexyl acetate or butyl acetate); and combinations and mixtures thereof.

Suitable co-solvents include polyhydric alcohols, which include glycols, triols and polyols such as ethylene glycol, diethylene glycol, propylene glycol, dipropylene glycol, trimethylene glycol, butylene glycol, polyethylene glycol, hexylene glycol, polyoxethylene, glycerin, trimethylpropane, sorbitol, polyvinylpyrrolidone, and the like.

Further suitable co-solvents include glycol ethers such as ethylene glycol monoethyl ether, glycol esters, glycol ether esters such as ethylene glycol monoethyl ether acetate and ethylene glycol diacetate; saturated and unsaturated fatty acids, mineral oil, silicone fluid, lecithin, retinol derivatives and the like, and ethers, esters and alcohols of fatty acids.

Although the exact amount of co-solvents that may be used in the adhesive matrix composition depends on the nature and amount of the other ingredients, such amount typically ranges from about 0.1% to about 40%, and preferably from about 0.1% to about 30% by weight, and more preferably from about 1% to about 20%, by weight based on the dry weight of the total adhesive matrix composition.

In certain embodiments of the invention, a permeation enhancer is incorporated into the adhesive matrix composition. The term "permeation enhancer" as used herein refers to substances used to increase permeability and/or accelerate the delivery of an active agent through the skin or mucosa, and include monhydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearly) including polyoxyethylene (4) lauryl ether, polyoxyethylene (2) oleyl ether and polyoxyethylene (10) oleyl ether commercially available under the trademark BRIJ® 30, 93 and 97 from ICI Americas, Inc., and BRIJ® 35, 52, 56, 58, 72, 76, 78, 92, 96, 700 and 721; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered and esters of sorbitol and sorbitol anhydride such as polysorbate 20 commercially available under the trademark Tween® 20 from ICI Americas, Inc., as well as other polysorbates such as 21, 40, 60, 61, 65, 80, 81, and 85. Other suitable enhancers include oleic and linoleic acids, triacetin, ascorbic acid, panthenol, butylated hydroxytoluene, tocopherol, tocopherol acetate, tocopheryl linoleate. If permeation enhancers are incorporated into the adhesive matrix composition, the amount typically ranges up to about 30%, and preferably from about 0.1% to about 15%, by weight based on the dry weight of the total adhesive matrix composition.

In addition to permeation enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenes, silicone fluid, mineral oil and hydrogenated wood rosins. Additional additives include binders such as lecithin which "bind" the other ingredients, or rheological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the final composition. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the carrier composition. Such additives or excipients are typically used in amounts up to 25%, and preferably from about 0.1% to about 10%, by weight based on the dry weight of the total adhesive matrix composition.

The adhesive matrix compositions according to the present invention can be prepared by first mixing appropriate amounts of the polymeric plastic material in volatile polar and/or non-polar organic liquids, such as those previously described as suitable volatile solvents. Appropriate amounts of active agent(s) are then added to the mixture together with appropriate amounts of pressure-sensitive adhesive(s), solvent(s) and/or co-solvent(s), with or without enhancer(s), and thoroughly mixed. The mixture of the adhesive matrix composition is next formed into a film at ambient temperature, preferably by coating or casting at a controlled specified thickness onto a flexible sheet material, such as a release liner, followed by evaporation of the volatile solvents at elevated temperatures (e.g., by passing through an oven). The non-volatile or higher boiling point solvents and/or co-solvents, such as the polyols, used in the carrier composition remain therein. The carrier composition has been coated or cast on the flexible sheet material, is then laminated to another flexible sheet material preferably a backing layer. Appropriate size and shape individual transdermal drug delivery systems are cut and then packaged (e.g., pouched).

The order of steps, the amount of the ingredients, and the amount and time of mixing may be important process variables which will depend on the specific polymers, active agents, solvents and/or co-solvents, enhancers and additives and excipients used in the composition. These factors can be adjusted by those skilled in the art, while keeping in mind the objects of achieving a solubilized active agent and providing a uniform product that will also give desirable results.

Reference to FIG. 1 shows a matrix-type transdermal drug delivery system 10 comprising a pressure-sensitive adhesive matrix composition layer 11, a release liner 12, and a backing layer 13. Removal of the release liner 12 exposes the pressure-sensitive adhesive matrix composition for topical application to the user.

Further details and examples of pressure-sensitive adhesives, enhancers, solvents, co-solvents, release liners, backing layers, and other additives, as well as transdermal systems generally, suitable in practicing the invention are described in U.S. Pat. Nos. 5,474,787 and 5,656,286, Ser. Nos. 09/161,312 and 60/115,927, all of which are assigned to Noven Pharmaceuticals, Inc. and incorporated herein by reference.

EXAMPLES

The above description and following specific examples are hereby illustrative of pharmaceutically acceptable matrix compositions and transdermal drug delivery systems, and methods of making same, within the contemplation of the invention. The description and examples are in no way intended to be, or should be considered, limiting of the scope of the invention. And while efforts have been made to ensure accuracy with respect to numbers used (such as amounts and temperatures), some experimental error and deviation should be accounted for and/or allowed.

Example 1

An estradiol/norethindrone acetate pressure-sensitive adhesive matrix composition was prepared by combining 0.7 parts of estradiol and 3.0 parts of norethindrone acetate along with 3.0 parts of ethyl cellulose (Ethocele® 10, Dow Chemical Corp., Midland, Mich.) in 30.0 parts ethyl acetate, 15.0 parts of toluene and 10.0 parts isopropyl alcohol. Then 12.2 parts of a polyacrylate adhesive (DURO-TAIE® 87–2510; National Starch Company, Bridgewater, N.J.) and 109.2 parts of a polysiloxane adhesive (BIO-PSA® Q7-4603; Dow Corning Corp, Midland, Mich.) were added and thoroughly mixed. Finally 9.0 parts of dipropylene glycol and 6.0 parts oleyl alcohol were added and mixed thoroughly in an appropriate container until the mixture was completely homogenous. The resulting composition had the ingredient concentrations on a dry weight percent basis (i.e., after evaporation of volatile solvents) as shown below.

| INGREDIENT | DRUG WEIGHT % |
| --- | --- |
| Polysiloxane Adhesive (BIO-PSA ® 7-4603) | 66.3 |
| Polyacrylate Adhesive (DURO-TAK ® 87-2287) | 5.0 |
| Ethyl Cellulose (Ethocel ® 10) | 10.0 |
| Dipropylene Glycol | 9.0 |
| Olelyl Alcohol | 6.0 |
| Estradiol | 0.7 |
| Norethindrone Acetate | 3.0 |
|  | 100.0 |

Examples 2–9

In the following examples, the method of Example 1 was used with the appropriate amounts of starting materials to yield compositions having the following ingredient concentrations set forth in tabular form in TABLE II. Examples 2, 3, and 5 are presented as control formulations for comparative purposes, but are not within the scope of the invention in as much as the resulting adhesive matrix compositions do not contain a polymeric plastic material.

TABLE II

|  | Ex. 2 | Ex. 3 | Ex. 4 | Ex. 5 | Ex. 6 | Ex. 7 | Ex. 8 | Ex. 9 |
| --- | --- | --- | --- | --- | --- | --- | --- | --- |
| Polysiloxane Adhesive (BIO-PSA ® 7-4502) | 0.0 | 71.4 | 54.5 | 53.6 | 48.6 | 43.6 | 58.0 | 53.0 |
| Polysiloxane Adhesive (BIO-PSA ® 7-4603) | 66.3 | 0.0 | 0.0 | 0.0 | 0.0 | 0.0 | 0.0 | 0.0 |
| Polyacrylate Adhesive (DURO-TAK ® 87-2287) | 5.0 | 0.0 | 0.0 | 0.0 | 0.0 | 0.0 | 0.0 | 0.0 |
| Polyacrylate Adhesive (Gelva ® 788) | 0.0 | 5.0 | 5.0 | 20.0 | 20.0 | 20.0 | 5.0 | 5.0 |
| Ethyl Cellulose (Ethocel ® 10) | 0.0 | 0.0 | 15.0 | 0.0 | 0.0 | 0.0 | 10.0 | 15.0 |
| Ethyl Cellulose (Ethocel ® 20) | 0.0 | 0.0 | 0.0 | 0.0 | 5.0 | 10.0 | 0.0 | 0.0 |
| Polyvinyl pyrrolidone (KOLLIDON ® 30) | 0.0 | 10.0 | 10.0 | 10.0 | 10.0 | 10.0 | 10.0 | 10.0 |
| Polyvinyl pyrrolidone (KOLLIDON ® 90) | 10.0 | 0.0 | 0.0 | 0.0 | 0.0 | 0.0 | 0.0 | 0.0 |
| Dipropylene Glycol | 9.0 | 6.0 | 6.0 | 8.0 | 8.0 | 8.0 | 8.0 | 8.0 |
| Oleyl Alcohol | 6.0 | 6.0 | 6.0 | 6.0 | 6.0 | 6.0 | 6.0 | 6.0 |
| Estradiol | 0.7 | 1.6 | 3.5 | 2.4 | 2.4 | 2.4 | 3.0 | 3.0 |
| Norethindrone Acetate | 3.0 | 0.0 | 0.0 | 0.0 | 0.0 | 0.0 | 0.0 | 0.0 |

What is claimed is:

1. A transdermal delivery system for providing drug delivery across skin in a mammal comprising:
   (a) a pharmaceutically acceptable pressure-sensitive adhesive matrix consisting essentially of a blend of:
      (i) one or more adhesives selected from the group consisting of polyacrylates, polysiloxanes, polyisobutylene, polyisoprene, styrenes, styrene block copolymers and block amide copolymers in an amount from 20% to 75% by weight based on the dry weight of the total adhesive matrix composition,
      (ii) an insoluble, non-adhesive ethyl cellulose polymer having a solution viscosity in the range of 3 cps to 40 cps, alone or in combination with an insoluble, non-adhesive cellulose ester in a total amount from 2.5% to 20% by weight based on the dry weight of the total adhesive matrix composition,
      (iii) at least one hydrophobic active agent,
      (iv) a hydrophilic crystallization inhibitor selected from the group consisting of soluble polyvinylpyrrolidone, soluble cellulose and cellulose derivatives, and polyethylene oxide in an amount from 5% to 15% by weight based on the dry weight of the total adhesive matrix composition,
      (v) a drug permeation enhancer in an amount up to 15% by weight based on the dry weight of the total adhesive matrix composition, and
      (vi) a polyhydric alcohol solvent in an amount up to 20% by weight based on the dry weight of the total adhesive matrix composition;
   wherein the adhesive matrix is capable of delivering the active agent at a substantially zero-order kinetic rate for period of time in excess of 72 hours.

2. The transdermal system according to claim 1, wherein the ethyl cellulose polymer has a solution viscosity in the range of 3 cps to 22 cps.

3. The transdermal system according to claim 1, wherein the ethyl. cellulose polymer is combined with an insoluble, non-adhesive cellulose ester selected from the group consisting of cellulose acetate butyrate and cellulose acetate propionate.

4. The transdermal system according to claim 1, wherein the hydrophilic crystallization inhibitor is soluble polyvinylpyrrolidone.

5. The transdermal system according to claim 1, wherein the one or more active agents are selected from the group consisting of steroidal and hormonal agents.

6. The transdermal system according to claim 5, wherein tie adhesives consist of 5%–40% by dry weight polyacrylate adhesive and 30%–90% by dry weight polysiloxane adhesive, the polydric alcohol solvent is dipropylene glycol in an amount of 5%–10% by dry weight, the permeation enhancer is oleyl alcohol in an amount of 1%–10% by dry weight, the hydrophilic crystallization inhibitor is soluble polyvinylpyrrolidone in an amount of 5%–15% by dry weight, and the hormonal agent consists of 17 β-estradiol in an amount of 0.1%–5% by dry weight alone or in combination with norethindrone acetate in an amount of 1%–7% by dry weight, said weights based on the dry weight of the total composition.

* * * * *